(12) United States Patent
Watson et al.

(10) Patent No.: US 8,217,171 B2
(45) Date of Patent: *Jul. 10, 2012

(54) ANTIVIRAL AGENTS

(75) Inventors: Keith Watson, Surrey Hills (AU); Guy Krippner, Glen Waverley (AU); Pauline Stanislawski, Craigieburn (AU); Darryl McConnell, Vienna (AT)

(73) Assignee: Biota Scientific Management Pty. Ltd., Notting Hill (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/100,931

(22) Filed: May 4, 2011

(65) Prior Publication Data

US 2011/0212966 A1    Sep. 1, 2011

Related U.S. Application Data

(60) Continuation of application No. 12/113,718, filed on May 1, 2008, now Pat. No. 7,951,955, which is a division of application No. 11/559,242, filed on Nov. 13, 2006, now Pat. No. 7,579,465, which is a division of application No. 10/450,005, filed as application No. PCT/AU01/01627 on Dec. 18, 2001, now Pat. No. 7,166,604.

(30) Foreign Application Priority Data

Dec. 18, 2000    (AU) .................................. PR2137/00

(51) Int. Cl.
*C07D 401/14* (2006.01)
*C07D 403/14* (2006.01)
*A61K 31/4523* (2006.01)
*A61P 31/12* (2006.01)

(52) U.S. Cl. ................ 544/238; 514/252.05; 514/252.11
(58) Field of Classification Search .................. 544/238; 514/252.05, 252.11
See application file for complete search history.

(56) References Cited

U.S. PATENT DOCUMENTS

| | | | |
|---|---|---|---|
| 3,997,565 A | 12/1976 | Kauer .......................... | 260/340.3 |
| 4,268,678 A | 5/1981 | Diana et al. .................... | 548/247 |
| 4,451,476 A | 5/1984 | Diana ........................... | 424/272 |
| 4,472,416 A | 9/1984 | Stetter et al. ................... | 424/269 |
| 4,843,087 A | 6/1989 | Diana ........................... | 514/374 |
| 4,857,539 A | 8/1989 | Diana et al. .................... | 514/378 |
| 4,861,791 A | 8/1989 | Diana et al. .................... | 514/374 |
| 4,939,267 A | 7/1990 | Diana ........................... | 548/237 |
| 4,942,241 A | 7/1990 | Diana et al. .................... | 548/131 |
| 4,945,164 A | 7/1990 | Diana ........................... | 548/247 |
| 4,956,351 A | 9/1990 | Mesens et al. .................... | 514/58 |
| 4,992,433 A | 2/1991 | Stokbroekx et al. .......... | 514/212 |
| 5,001,125 A | 3/1991 | Stokbroekx et al. .......... | 514/252 |
| 5,002,960 A | 3/1991 | Diana ........................... | 514/378 |
| 5,051,437 A | 9/1991 | Diana ........................... | 514/365 |
| 5,070,090 A | 12/1991 | Stokbroekx et al. ....... | 514/236.5 |
| 5,100,893 A | 3/1992 | Stokbroekx et al. .......... | 514/252 |
| 5,106,973 A | 4/1992 | Stokbroekx et al. .......... | 544/238 |
| 5,110,821 A | 5/1992 | Diana ........................... | 514/364 |
| 5,112,825 A | 5/1992 | Stokbroekx et al. .......... | 514/253 |
| 5,175,178 A | 12/1992 | Diana et al. .................... | 514/364 |
| 5,196,535 A | 3/1993 | Stokbroekx et al. .......... | 546/209 |
| 5,231,184 A | 7/1993 | Stokbroekx et al. .......... | 546/209 |
| 5,242,924 A | 9/1993 | Diana ........................... | 514/252 |
| 5,349,068 A | 9/1994 | Diana et al. .................... | 548/131 |
| 5,364,865 A | 11/1994 | Diana ........................... | 514/318 |
| 5,453,433 A | 9/1995 | Aldous et al. ................. | 514/362 |
| 5,464,848 A | 11/1995 | Diana et al. .................... | 514/364 |
| 5,514,679 A | 5/1996 | Aldous et al. ................. | 514/247 |
| 5,514,692 A | 5/1996 | Aldous et al. ................. | 514/314 |
| 5,523,312 A | 6/1996 | Aldous et al. ................. | 514/364 |
| 5,552,420 A | 9/1996 | Aldous et al. ................. | 514/364 |
| 5,567,717 A | 10/1996 | Aldous et al. ................. | 514/336 |
| 5,567,719 A | 10/1996 | Aldous et al. ................. | 514/342 |
| 5,618,821 A | 4/1997 | Aldous et al. ................. | 514/277 |
| 5,643,929 A | 7/1997 | Diana et al. .................... | 514/364 |
| 5,650,419 A | 7/1997 | Aldous et al. ................. | 514/363 |
| 5,665,763 A | 9/1997 | Aldous et al. ................. | 514/461 |
| 5,721,261 A | 2/1998 | Aldous et al. ................. | 514/364 |
| 5,750,527 A | 5/1998 | Aldous et al. ................. | 514/252 |
| 5,763,461 A | 6/1998 | Aldous et al. ................. | 514/340 |
| 5,821,257 A | 10/1998 | Aldous et al. ................. | 514/363 |
| 5,846,986 A | 12/1998 | Aldous et al. ................. | 514/364 |
| 7,166,604 B2 * | 1/2007 | Watson et al. ............ | 514/252.03 |

(Continued)

FOREIGN PATENT DOCUMENTS

EP    62-252783 A    11/1987

(Continued)

OTHER PUBLICATIONS

Hayden, F. G., Review in Medical Virology, 14, 17-31, 2004.*
Griffiths, P.A. Journal of Virology, 46, 3-8, 2009.*
Adams and Merluzzi (eds.), "The Search for Antiviral Drugs: Case Histories from Concept to Clinic," Birkhouse, Boston, 1993, Chapter 8, pp. 179-209.
Banker et al., eds., "Modern Pharmaceutics, 3d ed.", Marcel Dekker, New York, 1996, p. 596.
Diana et al., "Antipicornavirus Drugs: Current Status," *Antiviral Chemistry and Chemotherapy* 8(5): 401-408, 1997.
Hayden et al., "Intranasal Pirodavir (R77,975) Treatment of Rhinovirus Colds," *Antimicrobial Agents and Chemotherapy* 39(2): 290-294, Feb. 1995.
Hayden et al., "Safety and Efficacy of Intranasal Pirodavir (R77975) in Experimental Rhinovirus Infection," *Antimicrobial Agents and Chemotherapy* 36(4): 727-732, Apr. 1992.

(Continued)

*Primary Examiner* — Venkataraman Balasubramanian
(74) *Attorney, Agent, or Firm* — Seed IP Law Group PLLC

(57) ABSTRACT

This invention relates to compounds of formula I

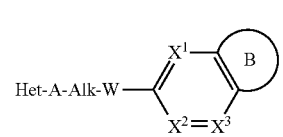

their salts, and pharmaceutically acceptable derivatives thereof, pharmaceutical compositions comprising these compounds and their use in the treatment of picornavirus infections in mammals, as well as novel intermediates useful in the preparation of the compounds of formula I.

14 Claims, No Drawings

U.S. PATENT DOCUMENTS

| | | | | |
|---|---|---|---|---|
| 7,579,465 | B2 * | 8/2009 | Watson et al. | 544/180 |
| 7,829,705 | B2 * | 11/2010 | Watson et al. | 544/238 |
| 7,951,955 | B2 * | 5/2011 | Watson et al. | 548/221 |

FOREIGN PATENT DOCUMENTS

| | | |
|---|---|---|
| EP | 0 248 253 A2 | 12/1987 |
| EP | 0 290 906 | 11/1988 |
| EP | 0 435 381 B1 | 7/1991 |
| EP | 0 398 425 B1 | 3/1994 |
| EP | 0 398 427 B1 | 3/1994 |
| EP | 1 300 398 A1 | 4/2003 |
| JP | 1-207278 A | 8/1989 |
| JP | 2104584 A | 4/1990 |
| JP | 3-47174 A | 2/1991 |
| JP | 3-47182 A | 2/1991 |
| JP | 3-56484 | 3/1991 |
| JP | 3-200771 A | 9/1991 |
| JP | 4-128283 A | 4/1992 |
| JP | 5-320117 | 12/1993 |
| JP | 8-81314 | 3/1996 |
| JP | 2000-500773 A | 1/2000 |
| JP | 2003-517481 A | 5/2003 |
| WO | WO 90/01874 | 3/1990 |
| WO | WO 95/04723 A1 | 2/1995 |
| WO | WO 96/04270 A1 | 2/1996 |
| WO | WO 97/23216 A1 | 7/1997 |
| WO | WO 97/46236 A1 | 12/1997 |
| WO | WO 98/11095 A1 | 3/1998 |
| WO | WO 98/17631 | 4/1998 |
| WO | WO 98/55120 A1 | 12/1998 |
| WO | WO 99/24440 A1 | 5/1999 |
| WO | WO 99/55663 A1 | 11/1999 |
| WO | WO 99/59587 A1 | 11/1999 |
| WO | WO 00/18761 A1 | 4/2000 |
| WO | WO 00/21927 A2 | 4/2000 |
| WO | WO 01/38313 A1 | 5/2000 |
| WO | WO 01/38314 A1 | 5/2000 |
| WO | WO 00/78746 A1 | 12/2000 |
| WO | WO 01/19822 A1 | 3/2001 |
| WO | WO 01/43740 A1 | 6/2001 |

OTHER PUBLICATIONS

Malamas et al., "Azole Phenoxy Hydroxyureas as Selective and Orally Active Inhibitors of 5-Lipoxygenase," *J. Med. Chem.* 39: 237-425, 1996.

Patani et al., "Bioisosterism: a Rational Approach in Drug Design," *Chemical Reviews* 96(8): 3147-3176, Dec. 1996.

Starling et al., "Anti-Inflammatory & Anti-Arrhythmic Activities of I-(Alkanoylphenoxy/Thiophenoxy)-3-(N4-phenylpiperazinyl)propanes," *Indian Journal of Chemistry* 15B: 715-719, Aug. 1977.

Strupczewski et al., "3-[[(Aryloxy)alkyl]piperidinyl]-1,2-Benzisoxazoles as D2/5-Ht2 Antagonists with Potential Atypical Antipsychotic Activity: Antipsychotic Profile of Iloperidone (HP 873)," *J. Med. Chem.* 38: 1119-1131, 1995T.

Wolff, ed., "Burger's Medicinal Chemistry, 5th Ed., vol. I: Principles and Practice," John Wiley & Sons, New York, 1995, pp. 975-977.

Zhao et al., "Design, Synthesis, and in Vitro Biological Activity of Benzimidazole Based Factor Xa Inhibitors," *Bioorganic & Medicinal Chemistry Letters* 10: 963-966, 2000.

* cited by examiner

ANTIVIRAL AGENTS

CROSS-REFERENCES TO RELATED APPLICATIONS

This application is a continuation of U.S. application Ser. No. 12/113,718 filed May 1, 2008 (allowed); which is a divisional of U.S. patent application Ser. No. 11/559,242 filed Nov. 13, 2006 (U.S. Pat. No. 7,579,465); which is a divisional of U.S. patent application Ser. No. 10/450,005, filed Oct. 17, 2003 (U.S. Pat. No. 7,166,604); which is a U.S. National Stage of PCT/AU01/001627, filed Dec. 18, 2001, which claims priority to Australian Application No. PR2137/00, filed Dec. 18, 2000; these applications are incorporated herein by reference in their entireties.

BACKGROUND

1. Technical Field

This invention relates to antiviral agents, in particular to compounds useful in the treatment of infections caused by Picornaviridae, such as human rhinovirus (HRV), and methods for their preparation. The invention also relates to the use of these compounds in the treatment of picornavirus infections and to intermediates useful in the preparation of these compounds. The compounds of the invention are especially suitable for use in the treatment of HRV and accordingly it will be convenient to describe the invention in connection with these viruses. However, it is to be understood that the invention is also applicable to other viruses of the Picornavirus family.

2. Description of the Related Art

Human rhinoviruses are a member of the genus Rhinovirus of the picornavirus family and are believed to be responsible for between 40 and 50% of common cold infections. Human rhinoviruses comprise a group of over 100 serotypically distinct viruses and accordingly antiviral activity for multiple serotypes and potency are considered to be equally important factors in drug design.

Two cellular receptors have been identified to which almost all typed HRVs bind. The major group, which comprises 91 of the more than 100 typed serotypes, binds to the intracellular adhesion molecule-1 (ICAM-1) while the minor group, which comprises the rest of typed serotypes with the exception of HRV87, binds to the low density lipoprotein receptor family of proteins.

Another genus of the Picornaviridae family is represented by the Enteroviruses. This genus includes polioviruses 1-3, coxsackieviruses A (23 serotypes) and B (6 serotypes), echoviruses (31 serotypes) and numbered enteroviruses 68-71. The clinical syndromes caused by enteroviruses include poliomyelitis, meningitis, encephalitis, pleurodynia, herpangina, hand foot and mouth disease, conjunctivitis, myocarditis and neonatal diseases such as respiratory illnesses and febrile illnesses.

Viruses of the Picornavirus family are characterized by a single stranded (+) RNA genome encapsidated by a protein shell (or capsid) having pseudo icosahedral symmetry. The surface of the capsid contains "canyons" which surround each of the icosahedral fivefold axes, and it is believed that the cellular receptors bind to residues on the canyon floor.

A hydrophobic pocket lies underneath the canyon within which a number of antiviral compounds are capable of binding, sometimes with consequential conformational changes. Some of these compounds have been shown to inhibit the uncoating of HRVs and, for some of the major receptor group viruses, inhibition of cell receptor binding has also been demonstrated. It has also been shown that when a compound is bound within the hydrophobic capsid pocket, HRVs are more stable to denaturation by heat or acids.

Examples of antipicornaviral compounds believed to act by binding within the hydrophobic pockets of the picornavirus capsid are described in U.S. Pat. Nos. 4,857,539, 4,992,433, 5,026,848, 5,051,515, 5,100,893, 5,112,825, 5,070,090, and Australian Patent No. 628172. One compound that has been the subject of recent human clinical trials is ethyl 4-[2-[1-(6-methyl-3-pyridazinyl)-4-piperidinyl]-ethoxy]benzoate, otherwise known as "Pirodavir". ("Intranasal Pirodavir (R77,975) Treatment of Rhinovirus Colds" F. G. Hayden, et al., *Antimicrobial Agents and Chemotherapy*, 39, 290-294, 1995.)

BRIEF SUMMARY

A novel class of antiviral compounds has now been discovered which has been found to exhibit particularly favorable antipicornaviral properties.

Accordingly the present invention provides a compound of formula I

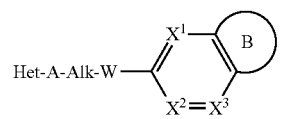

I its salts, and pharmaceutically acceptable derivatives thereof where:

Het is an optionally substituted 5- or 6-membered monocyclic heterocyclic radical or an optionally substituted 9- or 10-membered bicyclic heterocyclic radical;

A is O, S, NH, N($C_{1-6}$alkyl), $CH_2O$, a direct bond or a bivalent heterocyclic radical of the formula

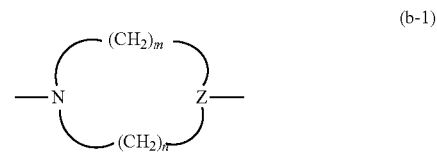

(b-1)

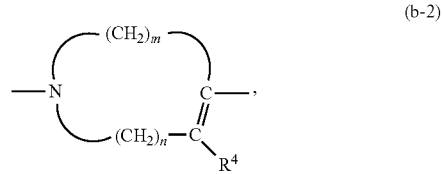

(b-2)

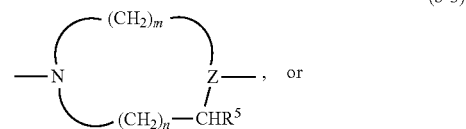

(b-3)

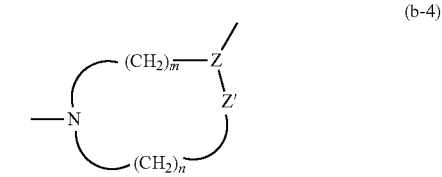

(b-4)

where one or more of the carbon atoms within the radicals (b-1) to (b-4) may be optionally substituted with $C_{1-6}$alkyl or two carbon atoms in the radicals (b-1) to (b-4) may be bridged with a $C_{2-4}$alkylene radical, m and n are each independently integers of 1 to 4 inclusive with the proviso that the sum of m and n in radicals (b-1) to (b-4) is 3, 4 or 5;

Z is N or $CR^6$ where $R^6$ is hydrogen, hydroxy, $C_{1-6}$alkyl, $C_{1-6}$alkoxy or amino;

ZN is O, S, $CHR^7$ or $NR^8$ where $R^7$ is hydrogen, hydroxy, $C_{1-6}$alkyl, $C_{1-6}$alkoxy or amino and $R^8$ is hydrogen or $C_{1-6}$alkyl;

$R^4$ is hydrogen or $C_{1-6}$alkyl; and $R^5$ is hydrogen, hydroxy, $C_{1-6}$alkyl or $C_{1-6}$alkoxy;

Alk is $C_{1-7}$alkylene or a direct bond;

W is O, S, $OCH_2$, a direct bond or $NR^9$ where $R^9$ is hydrogen or $C_{1-6}$alkyl;

$X^1$, $X^2$ and $X^3$ are each independently selected from N and CR, where R is hydrogen, halogen, hydroxy, $C_{1-6}$alkyl or $C_{1-6}$alkoxy and B is a five or six membered unsaturated heterocyclic ring, substituted with at least one substituent selected from, $R^{10}$, $OR^{10}$, $SR^{10}$ and $NR^9R^{10}$ where $R^{10}$ is $C_{1-6}$alkyl, $haloC_{1-6}$alkyl, $C_{1-6}$ alkenyl, $haloC_{1-6}$ alkenyl, $C_{1-6}$ alkynyl or $haloC_{1-6}$ alkynyl, with the proviso that when Alk is a direct bond and A is O, S, $CH_2O$ or a direct bond, then W is not O, S, $OCH_2$ or a direct bond.

The term "heterocyclic radical" as used herein refers to mono or bicyclic rings or ring systems which include one or more heteroatoms selected from N, S and O. The rings or ring systems generally include 1 to 9 carbon atoms in addition to the heteroatom(s) and may be saturated, unsaturated, aromatic or pseudoaromatic.

Examples of 5-membered monocyclic heterocycles include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl and examples of 6-membered monocyclic heterocycles include pyridyl, pyrimidinyl, pyridazinyl, pyrazinyl and triazinyl, each of which may be optionally substituted with $C_{1-6}$alkyl, $C_{1-6}$alkoxy, $C_{3-6}$alkynyl, $C_{3-6}$alkynyl, halo, hydroxy, mercapto, trifluoromethyl, amino, cyano or mono or di($C_{1-6}$alkyl)amino. Examples of 9 and 10-membered bicyclic heterocycles include indolyl, benzofuranyl, benzothienyl, benzoxazolyl, benzothiazolyl, benzisoxazolyl, benzisothiazolyl, indazolyl, isoquinolinyl, quinolinyl, quinoxalinyl, cinnolinyl, phthalazinyl, quinazolinyl, benzotriazinyl and the like, each of which may be optionally substituted with $C_{1-6}$alkyl, $C_{1-6}$alkoxy, $C_{3-6}$alkynyl, $C_{3-6}$alkynyl, halo, hydroxy, mercapto, trifluoromethyl, amino, cyano or mono or di($C_{1-6}$alkyl)amino. Examples of preferred heterocyclic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines and quinoxalines. Particular examples of the group Het are radicals of formula (a-1) to (a-14) below:

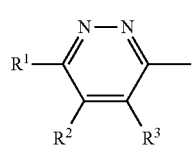

(a-1)

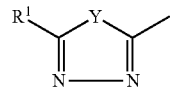

(a-2)

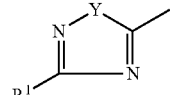

(a-3)

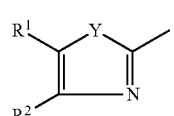

(a-4)

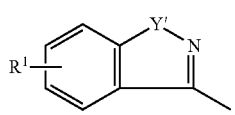

(a-5)

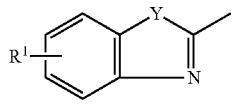

(a-6)

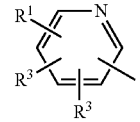

(a-7)

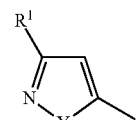

(a-8)

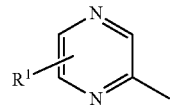

(a-9)

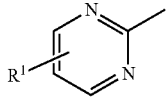

(a-10)

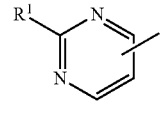

(a-11)

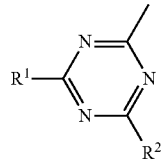

(a-12)

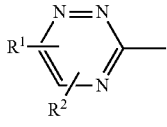

(a-13)

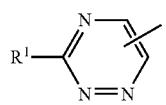
(a-14)

wherein $R^1$ is hydrogen, $C_{1-6}$ alkyl, halo, hydroxy, mercapto, halo$C_{1-6}$alkyl, amino, mono or di($C_{1-6}$alkyl)amino, cyano, formyl, $C_{1-6}$alkoxy, hydroxy$C_{1-4}$alkyl, $C_{1-4}$alkoxy$C_{1-4}$alkyl, $C_{1-6}$haloalkoxy, aryloxy, $C_{1-6}$alkylthio, arylthio, $C_{1-6}$alkylsulphinyl, $C_{1-6}$alkylsulphonyl, arylsulphinyl, arylsulphonyl, —CH=NO—$C_{1-4}$alkyl, $C_{1-6}$alkyloxycarbonyl, $C_{1-6}$alkylcarbonyl or aryl;

$R^2$ and $R^3$ are each independently selected from hydrogen, $C_{1-6}$alkyl, $C_{1-6}$alkoxy, halo or, in radicals (a-1), (a-4), (a-7) and (a-13), $R^1$ and $R^2$, or $R^2$ and $R^3$ combined may represent a bivalent radical of formula —CH=CH—CH=CH— or $(CH_2)_p$ where p is an integer from 2 to 4;

Y is O or S; and

YN is O, S, SO or $SO_2$.

The term "unsaturated five or six membered heterocyclic ring" as used herein for ring B refers to a 5 or 6 membered heterocyclic radical fused to the six-membered ring as depicted in Formula I. The ring includes one or more heteroatoms selected from N, S and O and will include 2 to 5 carbon atoms in addition to the heteroatom(s). Two of these carbon atoms are derived from the six-membered ring to which it is attached. The ring may be partially or fully saturated, and may be aromatic. The ring must contain at least one substituent selected from $R^{10}$, $OR^{10}$, $SR^{10}$ and $NR^9R^{10}$, where $R^9$ and $R^{10}$ are as defined above. Examples of unsaturated 5-membered heterocyclic rings include oxazole, thiazole, imidazole, 1,2,3-triazole, isoxazole, isothiazole, pyrazole, furan, thiophene and pyrrole, each of which in addition to the defined substituent may be optionally substituted with $C_{1-6}$alkyl, $C_{1-6}$alkoxy, $C_{3-6}$alkenyl, $C_{3-6}$alkynyl, halo, hydroxy, mercapto, trifluoromethyl, amino, cyano or mono or di($C_{1-6}$alkyl)amino. Examples of unsaturated 6-membered heterocyclic rings include pyridine, pyrimidine, pyrazine, pyridazine and 1,2,4-triazine, each of which in addition to the defined substituent may be optionally substituted with $C_{1-6}$alkyl, $C_{1-6}$alkoxy, $C_{3-6}$alkenyl, $C_{3-6}$alkynyl, halo, hydroxy, mercapto, trifluoromethyl, amino, cyano or mono or di($C_{1-6}$alkyl)amino. Particular examples of unsaturated five or six membered heterocyclic rings include radicals (c-1) to (c-11) below:

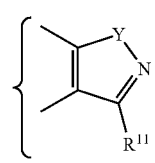
(c-1)

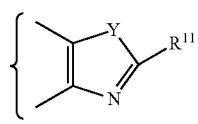
(c-2)

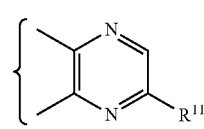
(c-3)

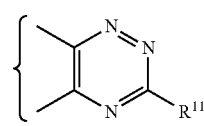
(c-4)

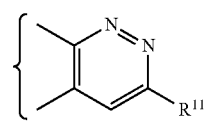
(c-5)

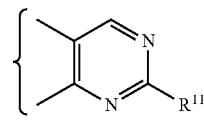
(c-6)

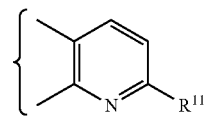
(c-7)

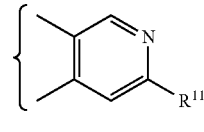
(c-8)

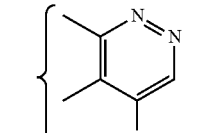
(c-9)

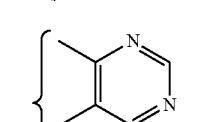
(c-10)

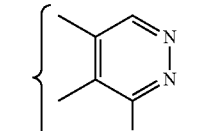
(c-11)

where Y is O, S or $NR^9$; and $R^{11}$ is $R^{10}$, $OR^{10}$, $SR^{10}$ or $NR^9R^{10}$, where $R^9$ and $R^{10}$ are as previously defined.

In some preferred embodiments of the invention one or more of the following definitions apply:

Het is a radical of formula (a-1), (a-2) or (a-8);

$R^1$ is hydrogen, methyl, ethyl, chloro, methoxy or trifluoromethyl;

$R^2$ and $R^3$ are each independently hydrogen, chloro or methyl;

Y is O or S;

A is O, NH, NMe, a bond, or a radical of formula (b-1);

Z is CH or N;

Alk is $C_{1-6}$alkylene or a direct bond;

W is O;

$X^1$, $X^2$ and $X^3$ are CH; and

B is (c-1) or (c-2).

As used herein, the term "$C_{1-6}$alkyl" as used alone or as part of a group such as "di($C_{1-6}$alkyl)amino" refers to straight chain, branched or cyclic alkyl groups having from 1 to 6 carbon atoms. Examples of such alkyl groups include methyl, ethyl, n-propyl, isopropyl, n-butyl, cyclopentyl and cyclohexyl. Similarly, $C_{1-4}$ alkyl refers to such groups having from 1 to 4 carbon atoms.

As used herein, the term "halo" as used alone or as part of a group such as "$C_{3-6}$halo alkenyl" refers to fluoro, chloro, bromo and iodo groups.

As used herein, the terms "$C_{1-6}$alkoxy" and "$C_{1-6}$alkyloxy" refer to straight chain or branched alkoxy groups having from 1 to 6 carbon atoms. Examples of $C_{1-6}$alkoxy include methoxy, ethoxy, n-propoxy, isopropoxy, and the different butoxy isomers.

As used herein, the term "$C_{3-6}$alkenyl" refers to groups formed from $C_{3-6}$ straight chain, branched or cyclic alkenes. Examples of $C_{3-6}$alkenyl include allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1,3-butadienyl, 1-4,pentadienyl, 1,3-cyclopentadienyl, 1,3-hexadienyl, 1,4-hexadienyl, 1,3-cyclohexadienyl and 1,4-cyclohexadienyl.

As used herein, the term "$C_{3-6}$alkynyl" refers to groups formed from $C_{3-6}$ straight chain or branched groups as previously defined which contain a triple bond. Examples of $C_{3-6}$alkynyl include 2,3-propynyl and 2,3- or 3,4-butynyl.

The term "optionally substituted" as used herein means that a group may include one or more substituents which do not interfere with the binding activity of the compound of formula I. In some instances the substituent may be selected to improve binding. Examples of optional substituents include halo, $C_{1-4}$alkyl, $C_{2-4}$alkenyl, $C_{2-4}$alkynyl, $C_{1-4}$alkoxy, halo$C_{1-4}$alkyl, hydroxy$C_{1-4}$alkyl, $C_{1-4}$alkoxy, $C_{1-4}$alkyl, hydroxy, aryl, amino, cyano, mercapto, $C_{1-4}$alkylamino, $C_{1-4}$dialkylamino, aryloxy, formyl, $C_{1-4}$alkylcarbonyl and $C_{1-4}$alkoxycarbonyl.

A particular group of compounds of the invention has the formula II:

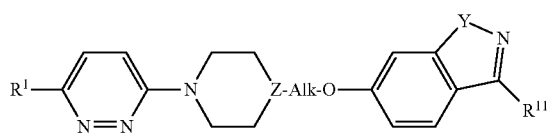

II wherein:

$R^1$ is hydrogen, $C_{1-4}$alkyl, halo, hydroxy, mercapto, trifluoromethyl, amino, mono or di($C_{1-4}$alkyl)amino, cyano, formyl, —CH=NO—$C_{1-4}$ alkyl, $C_{1-4}$alkoxy, $C_{1-4}$haloalkoxy, aryloxy, $C_{1-4}$alkylthio, or aryl;

Y is O, S, NH or NMe;

Z is CH or N;

Alk is $C_{1-6}$alkylene; and $R^{11}$ is $OR^{10}$ or $SR^{10}$, where $R^{10}$ is $C_{1-4}$alkyl.

Another particular set of compounds of the invention has the formula III:

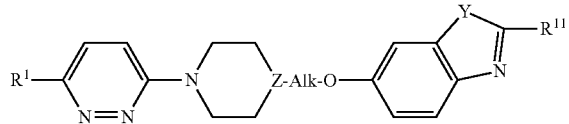

III wherein:

$R^1$ is hydrogen, $C_{1-4}$alkyl, halo, hydroxy, mercapto, trifluoromethyl, amino, mono or di($C_{1-4}$alkyl)amino, cyano, formyl, —CH=NO—$C_{1-4}$ alkyl, $C_{1-4}$alkoxy, $C_{1-4}$haloalkoxy, aryloxy, $C_{1-4}$alkylthio, or aryl;

Y is O, S, NH or NMe;

Z is CH or N;

Alk is $C_{1-6}$alkylene; and $R^{11}$ is $OR^{10}$ or $SR^{10}$, where $R^{10}$ is $C_{1-4}$alkyl.

Another particular set of compounds of the invention has the formula IV:

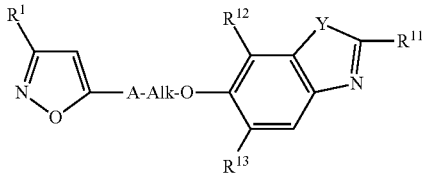

IV wherein:

$R^1$ is hydrogen, $C_{1-4}$alkyl, halo, hydroxy, mercapto, trifluoromethyl, amino, mono or di($C_{1-4}$alkyl)amino, cyano, formyl, —CH=NO—$C_{1-4}$alkyl, $C_{1-4}$alkoxy, $C_{1-4}$alkoxy$C_{1-4}$alkoxy, $C_{1-4}$haloalkoxy, aryloxy, $C_{1-4}$alkylthio, or aryl;

A is a bond or $CH_2O$;

Y is O, S, NH or NMe;

Alk is $C_{1-7}$alkylene;

$R^{11}$ is $OR^{10}$ or $SR^{10}$, where $R^{10}$ is $C_{1-4}$alkyl; and $R^{12}$ and $R^{13}$ are each independently hydrogen, halogen, $C_{1-4}$alkyl or $C_{1-4}$alkoxy.

A particular group of compounds of the invention has the formula V

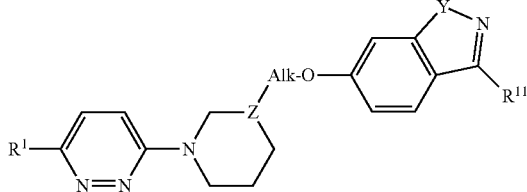

V wherein:

$R^1$ is hydrogen, $C_{1-4}$ alkyl, halo, hydroxy, mercapto, trifluoromethyl, amino, mono or di($C_{1-4}$ alkyl)amino, cyano, formyl, —CH=NO—$C_{1-4}$ alkyl, $C_{1-4}$ alkoxy, $C_{1-4}$haloalkoxy, aryloxy, $C_{1-4}$ alkylthio, or aryl;

Y is O, S, NH or NMc;

Z is CH or N;

Alk is $C_{1-6}$alkylene; and $R^{11}$ is $OR^{10}$ or $SR^{10}$, where $R^{10}$ is $C_{1-4}$alkyl.

A particular group of compounds of the invention has the formula VI:

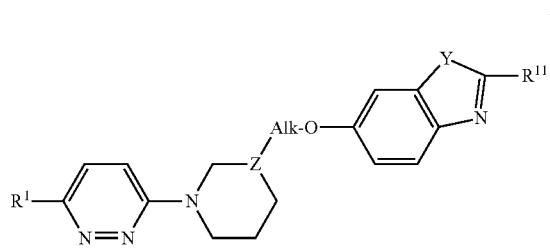

VI wherein:

R[1] is hydrogen, $C_{1-4}$ alkyl, halo, hydroxy, mercapto, trifluoromethyl, amino, mono or di($C_{1-4}$ alkyl)amino, cyano, formyl, —CH=NO—$C_{1-4}$ alkyl, $C_{1-4}$ alkoxy, $C_{1-4}$haloalkoxy, aryloxy, $C_{1-4}$ alkylthio, or aryl;

Y is O, S, NH or NMe;

Z is CH or N;

Alk is $C_{1-6}$alkylene; and

R[11] is OR[10] or SR[10], where R[10] is $C_{1-4}$alkyl.

A particular group of compounds of the invention has the formula VII

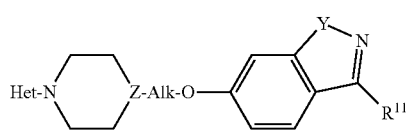

VII wherein:

Het is pyridyl, pyrazinyl, thiadiazolyl, benzoxazolyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy or hydroxy;

Y is O, S, NH or NMe;

Z is CH or N;

Alk is $C_{1-6}$alkylene; and

R[11] is OR[10] or SR[10] where R[10] is $C_{1-4}$alkyl.

A particular group of groups of the invention has the formula VIII:

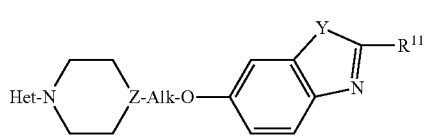

VIII wherein:

Het is pyridyl, pyrazinyl, thiadiazolyl, benzoxazolyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy or hydroxy;

Y is O, S, NH or NMe;

Z is CH or N;

Alk is $C_{1-6}$alkylene; and

R[11] is OR[10] or SR[10], where R[10] is $C_{1-4}$alkyl.

Another group of compounds of the invention has the formula IX

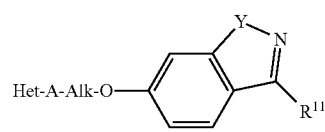

IX wherein:

Het is pyridyl, pyridazinyl, pyrazinyl, thiadiazolyl, benzoxazolyl, 1,2,4-triazinyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy or hydroxy;

A is a direct bond, O, NH or NMe;

Y is O, S, NH or NMe;

Alk is $C_{1-6}$ alkylene; and

R[11] is OR[10] or SR[10], where R[10] is $C_{1-4}$alkyl.

Yet another group of compounds of the invention has the formula X:

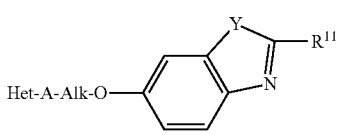

X wherein:

Het is pyridyl, pyridazinyl, pyrazinyl, thiadiazolyl, benzoxazolyl, 1,2,4-triazinyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy or hydroxy;

A is a direct bond, O, NH or NMe;

Y is O, S, NH or NMc;

Alk is $C_{1-6}$ alkylene; and

R[11] is OR[10] or SR[10], where R[10] is $C_{1-4}$alkyl.

Examples of specific compounds within the scope of the present invention are shown in Tables 1 and 5 below.

TABLE 1

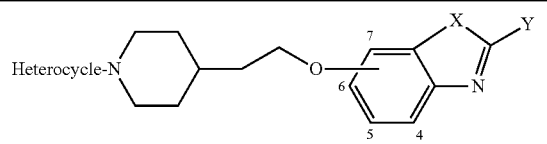

| Compd No. | Heterocycle | Position of linkage to benz-azole ring | X Group | Y-Substituent |
|---|---|---|---|---|
| 1 | 6-Me-3-Pyridazinyl | 6 | O | Methyl |
| 2 | 6-Me-3-Pyridazinyl | 5 | O | Methyl |
| 3 | 6-Me-3-Pyridazinyl | 6 | O | Ethyl |
| 4 | 6-Me-3-Pyridazinyl | 6 | O | Methylthio |
| 5 | 6-Me-3-Pyridazinyl | 6 | O | Ethoxy |
| 6 | 6-Cl-3-Pyridazinyl | 6 | O | Methylthio |
| 7 | 6-Me-3-Pyridazinyl | 6 | O | Ethylthio |
| 8 | 6-Cl-3-Pyridazinyl | 6 | O | Ethylthio |
| 9 | 5-Methyl-1,3,4-Thiadiazolyl | 6 | O | Ethylthio |
| 10 | 5-Methyl-1,3,4-Thiadiazolyl | 6 | O | Ethoxy |
| 11 | 6-Me-3-Pyridazinyl | 6 | O | n-Propoxy |
| 12 | 6-Me-3-Pyridazinyl | 6 | O | Methoxy |
| 13 | 6-Cl-3-Pyridazinyl | 6 | O | Ethoxy |
| 14 | 6-Me-3-Pyridazinyl | 6 | S | Methoxy |
| 15 | 6-Me-3-Pyridazinyl | 6 | S | Ethoxy |
| 16 | 6-Me-3-Pyridazinyl | 5/6 | NMe | Ethylthio |
| 19 | 6-Me-3-Pyridazinyl | 5 | S | Ethylthio |
| 20 | 6-Me-3-Pyridazinyl | 5 | S | n-Propoxy |

TABLE 1-continued

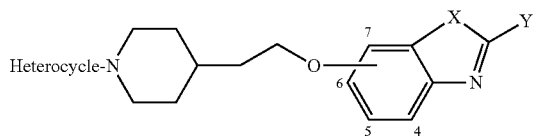

| Compd No. | Heterocycle | Position of linkage to benz-azole ring | X Group | Y-Substituent |
|---|---|---|---|---|
| 21 | 6-Me-3-Pyridazinyl | 5 | S | Ethoxy |
| 22 | 6-Me-3-Pyridazinyl | 5 | O | Ethylthio |
| 23 | 6-Me-3-Pyridazinyl | 5 | O | Ethoxy |
| 24 | 6-Me-3-Pyridazinyl | 6 | S | n-Propylamino |
| 25 | 6-Me-3-Pyridazinyl | 5 | NH | Ethylthio |
| 26 | 6-Me-3-Pyridazinyl | 6 | O | n-Butyl |
| 27 | 6-Me-3-Pyridazinyl | 6 | O | n-Propyl |
| 28 | 5,6-Me$_2$-3-Pyridazinyl | 6 | O | Ethoxy |
| 29 | 3-Me-1,2,4-Thiadiazol-5-yl | 6 | O | Ethoxy |
| 30 | 5,6-Me$_2$-1,2,4-Triazin-3-yl | 6 | O | Ethoxy |
| 31 | 1-Me-Tetrazol-5-yl | 6 | O | Ethoxy |
| 32 | 6-Cl-5-Me-3-Pyridazinyl | 6 | O | Ethoxy |
| 33 | 5-Me-3-Pyridazinyl | 6 | O | Ethoxy |

TABLE 2

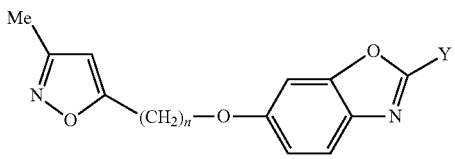

| Compound Number | Alkylene chain length n | Y Substituent |
|---|---|---|
| 17 | 3 | Ethylthio |
| 18 | 3 | Ethoxy |
| 34 | 5 | Ethoxy |

TABLE 3

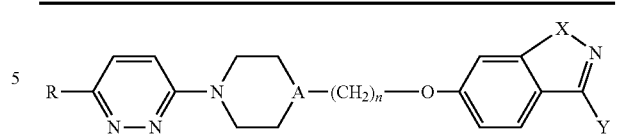

| Compound Number | R Substituent | Group A | Alkylene chain length n | Atom X | Group Y |
|---|---|---|---|---|---|
| 35 | Methyl | CH | 2 | O | Ethoxy |
| 36 | Methyl | CH | 2 | O | Ethyl |
| 37 | Chloro | CH | 2 | O | Ethoxy |
| 38 | Methyl | CH | 2 | O | n-Propoxy |
| 39 | Methyl | CH | 2 | O | n-Propyl |
| 40 | Methyl | CH | 2 | S | Ethoxy |
| 41 | Chloro | CH | 3 | O | Ethoxy |
| 42 | Methyl | N | 2 | O | Ethoxy |

TABLE 4

| Compound Number | X Substituent | Y Substituent |
|---|---|---|
| 43 | Ethoxy | H |
| 44 | Chloro | Chloro |
| 45 | Ethoxy | Ethoxy |
| 46 | H | Ethoxy |

TABLE 5

| Compound Number | Structure |
|---|---|
| 47 | 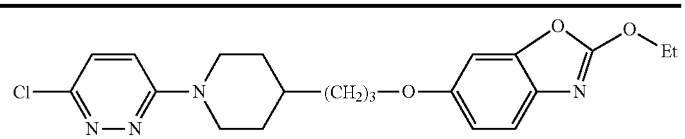 |
| 48 | 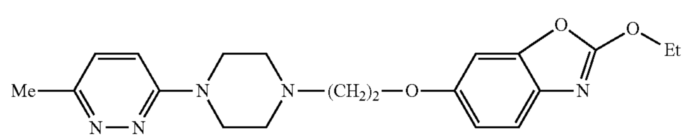 |
| 49 | 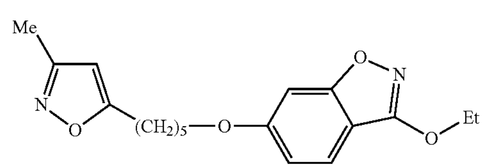 |
| 50 | 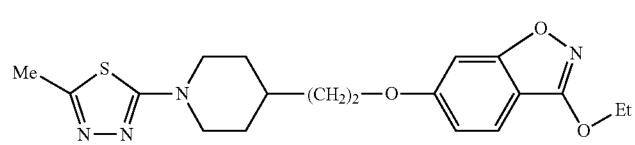 |

TABLE 5-continued

| Compound Number | Structure |
|---|---|
| 51 | 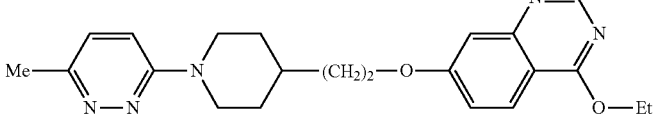 |
| 52 | 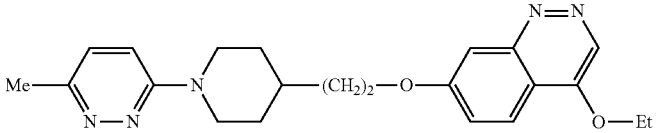 |
| 53 | 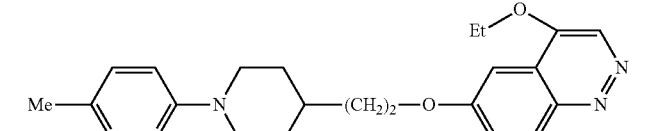 |
| 54 | 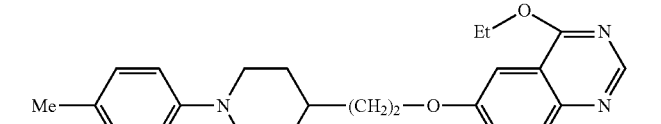 |
| 55 | 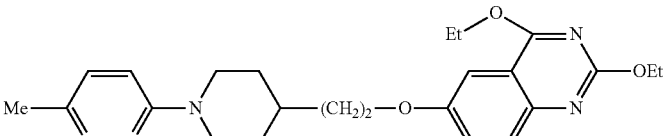 |
| 56 | 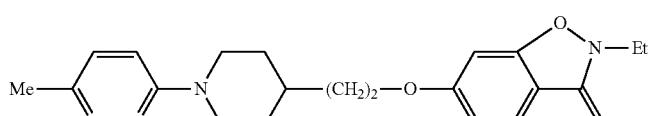 |
| 57 | 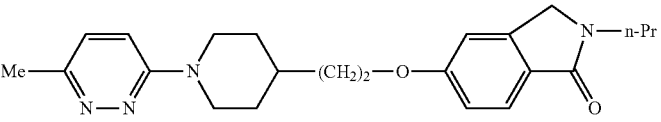 |
| 58 | 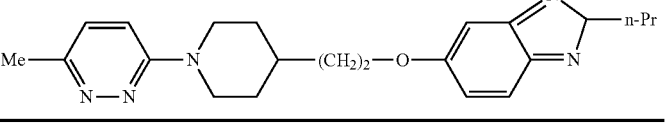 |

The compounds of the present invention may be prepared using methods analogous to those described in the prior art. For example, compounds in which the Het radical is of formula (a-1) may be prepared using methodology analogous to the processes described in U.S. Pat. Nos. 4,992,433, 5,112,825 and 5,100,893. Similarly, compounds in which Het is (a-2), (a-3), (a-4), (a-5) or (a-6) may be prepared using methodology similar to that described in U.S. Pat. No. 5,070,090 and Australian Patent No. 629172, and compounds in which Het is (a-7) or (a-8) may be prepared in accordance with methodology similar to that described in U.S. Pat. No. 5,364,865.

In one method the compounds of the present invention are prepared via an intermediate of formula XI:

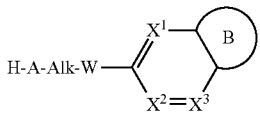

XI where A, Alk, W, Ar, $X^1$, $X^2$, $X^3$ and B are as described above.

This intermediate may be prepared using methodology similar to that described in U.S. Pat. No. 5,231,184. In one example intermediates of formula XI, when W is O, are prepared by the reaction of compounds of the formula P-A-Alk-OH or P-A-Alk-L with hydroxy aromatic compounds of formula XII.

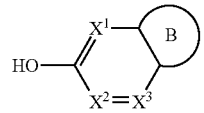

XII where Ar, $X^1$, $X^2$, $X^3$ and B are as defined above, P is H or a protecting group, and L is a leaving group. Removal of the protecting group P in the reaction product affords the reactive intermediates of formula XI.

Examples of suitable protecting groups P in compounds of formula P-A-Alk-OH or P-A-Alk-L include benzyl or acyl moieties which can be introduced and removed by standard methods (see, "Protective Groups in Organic Synthesis", Theodora Green, Wiley Interscience, 1981).

The intermediate of formula XI may be reacted with a compound of formula Het-L, where Het is as defined above and L is a suitable leaving group to afford a compound of formula I. Where this reaction is an N-alkylation reaction, it can be conducted using procedures known to the art, such as under the conditions described in U.S. Pat. No. 5,231,184 for performing analogous N-alkylations. In performing the reaction described above it may be necessary to protect one or more substituents on groups such as $X^1$, $X^2$, $X^3$ or B.

Some of the intermediates of formula XI and XII are novel and represent a further aspect of the present invention.

Examples of suitable leaving groups include halogen, such as fluoro, chloro, bromo and iodo, and halogen-like groups such as p-toluenesulphonyloxy and methanesulphonyloxy.

An additional method of preparing certain compounds of the invention of formula Ia (Compounds for formula I where W=O) involves condensing a compound of formula XIII with a suitable precursor of formula XII:

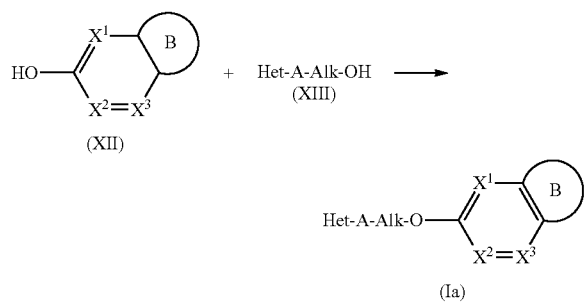

using Mitsunobu Reaction conditions (see Chemical Syntheses, Vol. 42, p 335, 1992) and where Het, A, Alk, $X^1$, $X^2$, $X^3$ and B are as defined for formula I.

Intermediates of formula XII may often be prepared from protected forms of the hydroxy compound. For example compounds of formula XII wherein $X^1$-$X^3$ are CH (hereinafter referred to as compounds of formula (XIIa)) can be made from the corresponding compounds which have an alkoxy or benzyloxy substituent which can be converted to OH by routine deprotection reagents including HBr or $BBr_3$.

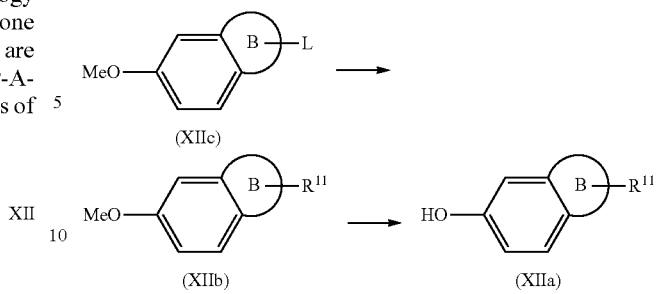

The chemical literature contains many references to the preparation of compounds of formula (XIIb) including, for example, U.S. Pat. No. 5,919,807 and *J. Org. Chem.*, 61, 3289 (1996). Compounds of formula (XIIb) can generally be prepared from the corresponding compounds (XIIc), which have a leaving group L available for displacement by $R^{11}$ when $R^{11}$ is $OR^{10}$, $SR^{10}$ or $NR^9R^{10}$. There are several references in the literature to the preparation of examples of compounds of general formula (XIIc), for example in U.S. Pat. Nos. 5,919,807 and 5,747,498 and *J. Med. Chem.*, 24, 93 (1981).

Several references, including U.S. Pat. Nos. 5,112,825 and 5,242,924, describe methods for the preparation of various compounds of formula XIII.

The compounds of the present invention are useful in the prevention or treatment of picornoviral infections in mammals, particularly humans.

Accordingly, in a further aspect the invention provides a method for the treatment or prophylaxis of a picornaviral infection in a mammal including the step of administering an effective amount of a compound of formula I.

The picornavirus infection may be caused by any virus of the family Picornaviridae. Representative family members include human rhinoviruses, polioviruses, enteroviruses including coxsackieviruses and echoviruses, hepatovirus, cardioviruses, apthovirus, hepatitis A and other picornaviruses not yet assigned to a particular genus, including one or more of the serotypes of these viruses. Preferably the invention is used in the prevention or treatment of infection caused by one or more serotypes of rhinovirus.

Without wishing to be limited by theory, it is believed that the heteroatoms in the fused heterocyclic moiety of the compound of formula I may be involved in hydrogen bonding with an asparagine residue generally present near the opening of the hydrophobic pocket, and that this interaction enhances the binding of the compounds in the capsid pocket, relative to the prior art compounds. It is further believed that the fused heterocyclic moiety may be more resistant to hydrolysis and esterase activity than the ester bond of pirodavir, and that this may allow more flexibility in the methods of administration of the compound to the site of activity, than available for readily hydrolysable pirodavir. In particular it may allow oral administration of the compounds or reduce metabolism in the nasal mucosa following topical administration.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts. The pharmaceutically acceptable salts may include conventional non-toxic salts or quarternary ammonium salts of these compounds, which may be formed, e.g., from organic or inorganic acids or bases. Examples of such acid addition salts include, but are not limited to, those formed with pharmaceutically acceptable acids such as acetic, propionic, citric, lactic, methanesulphonic, toluenesulphonic, benzenesulphonic, salicyclic, ascorbic, hydrochloric, orthophosphoric, sulphuric and hydrobromic acids. Base salts includes, but is not limited to, those formed with pharmaceutically acceptable cations, such as sodium, potassium, lithium, calcium magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

The compounds of the invention may be in crystalline form or as solvates (e.g., hydrates) and it is intended that both forms are within the scope of the present invention. Methods of solvation are generally known within the art.

Pharmaceutically acceptable derivatives may include any pharmaceutically acceptable salt, hydrate or any other compound or prodrug which, upon administration to a subject, is capable of providing (directly or indirectly) a compound of formula I or an antivirally active metabolite or residue thereof.

Any compound that is a prodrug of a compound of formula I is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine.

It will be appreciated that some derivatives of the compound of formula I may have an asymmetric center, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates.

The invention also provides the use of a compound of formula I in the manufacture of a medicament for the treatment or prophylaxis of picornavirus infection.

While it is possible that, for use in therapy, a compound of the invention may be administered as the neat chemical, it is preferable to present the active ingredient as a pharmaceutical formulation.

In view of the general lipophilic nature of the compounds, they are particularly suitable to oral forms of administration; however, other forms of administration are also envisaged.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be acceptable in the sense of being compatible with the other ingredients of the formulation and not deleterious to the recipient thereof.

The compounds of this invention may also be useful in combination with known anti-viral or anti-retroviral agents or other pharmaceuticals used in the treatment of viral infections. Representative examples of these additional pharmaceuticals include immunomodulators, immunostimulants, antibiotics and anti-inflammatory agents. Exemplary antiviral agents include zanamivir, rimantidine, amantidine, ribavirin, AZT, 3TC, (−) FTC, acyclovir, famciclovir, penciclovir, ddI, ddC, ganciclovir, saquanivir, loviride, other non-nucleotide reverse transcriptase (RT) inhibitors and protease inhibitors, antiviral and antireceptor antibodies and receptor analogues, such as ICAM-1. Exemplary immunomodulators and immunostimulants include various interleukins, cytokines and antibody preparations. Exemplary antibiotics include antifungal agents and antibacterial agents. Exemplary anti-inflammatory agents include glucocorticoids and non-steroidal anti-inflammatory compounds.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate predetermined volume of the solution or suspension. In the case of a spray, this may be achieved for example by means of a metering atomizing spray pump. To improve nasal delivery and retention, the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size, for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Liquids or powders for intranasal administration, tablets or capsules for oral administration and liquids for intravenous administration are preferred compositions.

DETAILED DESCRIPTION

The invention will now be described with reference to the following examples which illustrate some preferred aspects of the present invention. However, it is to be understood that the particularity of the following description of the invention is not to supersede the generality of the preceding description of the invention.

EXAMPLES

Example 1

Preparation of 6-{2-[1-(6-Methyl-3-pyridazinyl)-4-piperidinyl]ethoxy}-2-methylthiobenzoxazole (Compound 4 from Table 1)

(a) Preparation of 2-mercapto-6-hydroxybenzoxazole (see also *J. Org. Chem.*, 19, 758)

A mixture of aminoresorcinol hydrochloride (1.1 g), potassium ethyl xanthate (1.2 g) and potassium carbonate (1.0 g) was dissolved in ethanol/water (1:1, 20 ml) and (under an argon balloon) heated under reflux for 3 hours. The pale yellow solution was cooled to RT and then acetic acid (2 ml) was added to make the solution slightly acidic (gas evolution). A cream precipitate soon formed and the sealed flask was kept in the fridge overnight. The cream solid was collected by filtration and the damp product (0.9 g) was used immediately in the next step.

(b) Preparation of 6-hydroxy-2-methylthiobenzoxazole

A mixture of 6-hydroxy-2-mercaptobenzoxazole (165 mg), sodium bicarbonate (84 mg) and dimethyl sulfate (94 μl) was dissolved in water (2 ml) with stirring and under an argon atmosphere. The reaction mixture was stirred at RT overnight and HPLC showed that all starting material was gone. The reaction mixture was evaporated to dryness to give a dark brown solid (one can also extract the reaction mixture with chloroform to give the crude product). Chromatography on silica gel using 10% ethyl acetate/hexane gave the pure product as a near-white crystalline solid (45 mg, 25%).

(c) Preparation of 2-Methylthio-6-[N-(6-methyl-3-pyridazinyl)piperidinyl-4-ethoxy]benzoxazole (Compound 4)

A mixture of 6-hydroxy-2-methylthiobenzoxazole (100 mg), 3-[4-(2-chloroethyl)-1-piperidinyl]-6-methylpyridazine (130 mg) and potassium carbonate (100 mg) was heated and stirred in DMF (3 ml) at 90-100° under argon for 20 hr. Tlc showed that the reaction was virtually complete and the DMF was removed under reduced pressure and the residue was partitioned between water and chloroform. The chloroform extracts were evaporated and the residue was chromatographed on silica/chloroform to give the product as a pale cream solid (110 mg, 50%). The $^1$H nmr spectrum is summarized in Table 6 below.

Example 2

Preparation of 2-Ethoxy-6-{2-[N-(6-methyl-3-pyridazinyl)piperidinyl]-4-ethoxy}benzoxazole (Compound No 5)

Sodium metal (100 mg) was dissolved in ethanol (5 ml) and the solution was added to a solution of the methylthiobenzoxazole (compound No. 4) (74 mg) in THF (2 ml). The resultant solution was stirred at RT for 24 hr when hplc indicated that all starting material had disappeared. The reaction mixture was evaporated to dryness and the residue was partitioned between water and dichloromethane. The crude organic product was purified by chromatography on silica/CH$_2$Cl$_2$ to give Compound No. 5 as a pale cream solid (46 mg). The $^1$H nmr and MS data are recorded in Table 6 below.

Example 3

Compounds No 1, 2, 3, 6, 7, 8, 9, 17, 19, 22, 25, 26, 27 were prepared by reacting the appropriate Het-A-Alk-Cl or Het-A-Alk-OH with the required 2-substituted 5- or 6-hydroxybenzazole (benzoxazole, benzothiazole or benzimidazole) following similar conditions to those described in Example 1 part (c). The $^1$H nmr and/or MS data are recorded in Table 6 below.

Example 4

The 2-alkoxybenz-azole derivatives, Compounds No 10, 11, 12, 13, 14, 15, 18, 20, 21, 23 were prepared from the corresponding 2-methylthio or 2-ethylthiobenzoxazole or benzothiazole by reaction with the appropriate sodium alkoxide following essentially the same conditions as described in Example 2. The $^1$H nmr and/or MS data are recorded in Table 6 below.

Example 5

Preparation of a mixture of 2-Ethylthio-3-Methyl-6-{2-[N-(6-methyl-3-pyridazinyl)piperidinyl]-4-ethoxy}benzimidazole and 2-Ethylthio-3-Methyl-5-{2-[N-(6-methyl-3-pyridazinyl)piperidinyl]-4-ethoxy}benzimidazole (Compound No 16)

Methylation of 2-ethylthio-5-hydroxybenzimidazole gave an approximately 1:1 mixture of 2-ethylthio-3-methyl-5-hydroxybenzimidazole and 2-ethylthio-3-methyl-6-hydroxybenzimidazole which could not be easily separated. Reaction of this mixture of hydroxy compounds with 3-[4-(2-chloroethyl)-1-piperidinyl]-6-methylpyridazine, following the method described in Example 1, gave a 1:1 mixture of isomeric products (Compound No 16).

Example 6

Preparation of 6-{2-[1-(6-Methyl-3-pyridazinyl)-4-piperidinyl]ethoxy}-3-ethoxy-1,2-benzisoxazole (Compound 35 from Table 3)

(a) Preparation of 2-hydroxy-4-methoxybenzohydroxamic acid according to literature procedure Chem. Ber. 100, 954-960 (1967)

An hydroxylamine solution was prepared by addition of aqueous sodium hydroxide (393 mg, 9.82 mmol)/water (1.6 ml) to a stirred solution of hydroxylamine hydrochloride (292 mg, 4.21 mmol) in water (3.5 ml). Immediately slowly added a solution of methyl 2-hydroxy-4-methoxybenzoate (511 mg, 2.81 mmol) in 1,4-dioxane (1.5 ml). The resulting reaction mixture was stirred at room temperature for 18 hours, under an argon atmosphere. The reaction mixture was concentrated on a rotary evaporator to half the original volume, and the product precipitated by addition of concentrated hydrochloric acid, keeping flask cool in an ice bath. Filtered the suspension to give 2-hydroxy-4-methoxybenzohydroxamic acid (476 mg, 92%) as a pale brown solid.

$^1$H nmr spectrum (CDCl$_3$) δ (ppm): 3.72 (s, 3H); 6.36 (m, 2H); 7.41 (d, 1H).

(b) Preparation of 3-hydroxy-6-methoxy-1,2-benzisoxazole

A solution of carbonyl diimidazole (1.07 g, 6.57 mmol) in anhydrous THF (8 ml) was added to a stirred boiling solution of the hydroxamic acid (602 mg, 3.29 mmol) in THF (6 ml). The resulting solution was heated at reflux for approx. 8-10 hours, then allowed to cool to room temperature and stirred overnight under an argon atmosphere. Thin layer chromatography (tlc) (silica; 1:1 hexane/ethyl acetate) showed minimal starting material and new non polar material. The solution was evaporated on a rotary evaporator to give an orange colored oil. Water (6 ml) was added, and contents cooled (ice bath) and acidified to pH 2 with concentrated hydrochloric acid. The crude, damp 3-hydroxy-6-methoxy-1,2-benzisoxazole precipitated as a cream orange solid (645 mg).

¹H nmr spectrum (CDCl₃) δ (ppm): 3.82 (s, 3H); 6.73 (fd, 1H); 6.80 (dd, 1H); 7.52 (d, 1H).
LCMS (ESI) 166 (M+1)⁺

(c) Preparation of
3-ethoxy-6-methoxy-1,2-benzisoxazole

Benzisoxazole from part (b) (193 mg, 1.17 mmol), ethanol (750, 1.29 mmol) and triphenylphosphine (460 mg, 1.75 mmol) were dissolved in anhydrous THF (4 ml) and cooled) (0°. Diisopropylazodicarboxylate (345 µl, 1.75 mmol) was added slowly and after 10-15 min the reaction flask was removed from the ice bath and the reaction mixture was stirred at room temperature overnight under an argon atmosphere. The solution was evaporated to dryness and the residue pre-absorbed onto silica, and chromatographed on silica (19 g); eluent: hexane (300 ml), 10-30% ethyl acetate/hexane to give 3-ethoxy-6-methoxy-1,2-benzisoxazole (101 mg, 44%) as white crystals.
¹H nmr spectrum (CDCl₃) δ (ppm): 1.50 (t, 3H); 3.87 (s, 3H); 4.47 (q, 2H); 6.86 (m, 2H), 7.47 (d, 1H).
LCMS (ESI) 194 (M+1)⁺

(d) Preparation of
3-ethoxy-6-hydroxy-1,2-benzisoxazole

Boron tribromide (1.0M solution in dichloromethane; 1.39 ml, 1.39 mmol) was added to a stirred, −78° cooled solution of benzisoxazole from part (c) (179 mg, 928 µmol) in dichloromethane (4 ml) under an argon atmosphere. The reaction mixture was gradually warmed to room temperature over approx. 2 hours, and stirred overnight. Tlc (silica, 2:1 hexane/ethyl acetate) showed new polar material as well as unreacted starting material. The reaction was worked up by adding water (5 ml) and ice. The aqueous phase was neutralized by addition of saturated NaHCO₃ solution, and saturated with NaCl. The aqueous phase was extracted into dichloromethane (3×60 ml), then the organic extracts combined and washed with brine (10 ml) and dried (NaSO₄). The product was purified by chromatography on silica (18 g; eluent 2.5%, 5%, then 15% ethyl acetate/hexane). The first compound to elute was unreacted 3-ethoxy-6-methoxy-1,2-benzisoxazole, (46 mg), followed by 3-ethoxy-6-hydroxy-1,2-benzisoxazole 108 mg (65%).
¹H nmr spectrum (CDCl₃) δ (ppm): 1.45 (t, 3H); 4.40 (q, 2H); 6.74 (m, 2H); 7.38 (m, 1H).
LCMS (ESI) 180 (M+1)⁺

(e) Preparation of Compound 35

A mixture of 2-[-1-(6-methyl-3-pyridazinyl)-4-piperidinyl]ethanol (42 mg, 188 µmol), benzisoxazole from part (d) (28 mg, 156 µmol) and polymer-supported triphenylphosphine (145 mg, 234 µmol) in anhydrous THF (3 ml) was cooled)(0° and stirred under an argon atmosphere. Neat diisopropylazodicarboxylate (46 µml, 234 µmol) was added slowly and the reaction mixture was allowed to warm to room temperature and stir overnight. The reaction mixture was filtered, then pre-adsorbed onto silica and chromatographed on silica (approx. 5 g); using firstly 2:1 hexane/ethyl acetate as eluent, then gradually increased to 70% ethyl acetate/hexane to afford Compound 35 (44 mg; 73%) as a white powder. The ¹H nmr and MS data are recorded in Table 6 below.

Example 7

Compounds No 36, 37, 38, 39, 40, 41, 42, 49, 50, 56 and 57 were prepared by reacting the appropriate Het-A-Alk-Cl or Het-A-Alk-OH with the required 3-substituted 6-hydroxy-1,2-benzisoxazole (or 1,2-benzisothiazole) following similar conditions to those described in Example 6. The ¹H nmr and/or MS data are recorded in Table 6 below.

Example 8

The n-propylaminobenzothiazole derivative, Compound No 24, was prepared from the corresponding 2-methoxybenzothiazole (Compound 14) by heating with excess n-propylamine. The ¹H nmr and/or MS data are recorded in Table 6 below.

Example 9

Preparation of 2-Ethoxy-6-{2-[N-(5,6-dimethyl-3-pyridazinyl)piperidinyl]-4-ethoxy}benzoxazole
(Compound No 28)

(a) Preparation of 2-ethoxy-6-hydroxybenzoxazole

A mixture of equivalent amounts of 4-aminoresorcinol hydrochloride and anhydrous sodium acetate in anhydrous ethanol was stirred for 16 hours at room temperature with a slight excess of tetraethyl orthocarbonate to give 2-ethoxy-6-hydroxybenzoxazole in 60% yield.
(b) Reaction of 2-ethoxy-6-hydroxybenzoxazole with 2-[-1-(5,6-dimethyl-3-pyridazinyl)-4-piperidinyl]ethanol was carried out using a Mitsunobu coupling and similar conditions to those described in Example 6 part (e). The ¹H nmr and/or MS data for Compound 28 are recorded in Table 6 below.

Example 10

Compounds No 29, 30, 31, 32, 33, 34, 47 and 48 were prepared by reacting the appropriate Het-A-Alk-Cl or Het-A-Alk-OH with 2-ethoxy-6-hydroxybenzoxazole following similar conditions to those described in Example 1, part (c) or Example 6 part (e). The ¹H nmr and/or MS data are recorded in Table 6 below.

Example 11

Preparation of 6-{2-[1-(6-methyl-3-pyridazinyl)-4-piperidinyl]ethoxy}-4-ethoxy-cinnoline (Compound 53 from Table 5)

(a) Preparation of 4-chloro-6-methoxycinnoline

6-Methoxy-4-hydroxycinnoline (Osborn, A. R. and Schofield, K. *J. Chem. Soc.*, 1955, 2100) was prepared from 2-amino-5-methoxyacetophenone by diazotisation.
Phosphorous oxychloride (5 ml) was added to a mix of dimethylaniline (157 mg, 1.3 mmol) and 6-methoxy-4-hydroxycinnoline (208 mg, 1.2 mmol). The reaction was heated at reflux for 15 min, then cooled and concentrated under vacuum. The residue was partitioned between chloroform (100 ml) and water (30 ml), then the organic layer was washed with brine and dried (Na₂SO₄). Chromatography of the residue adsorbed onto silica gel (3 g) on silica gel (15 g) eluent CH₂Cl₂ to 10% Ethylacetate/CH₂Cl₂ gave 6-methoxy-4-chlorocinnoline (135 mg, 0.7 mmol) in 59% yield as white yellow solid. δ_H(CDCl₃)=4.03 (s, 3H); 7.28 (d, 1H); 7.51 (dd, 1H); 8.41 (d, 1H) and 9.22 (br s, 1H). MS (ESI) (M+H)⁺ 195.

(b) Preparation of 4-chloro-6-hydroxycinnoline

A solution of 6-methoxy-4-chlorocinnoline (135 mg, 0.7 mmol) in toluene (7 ml) was added to a stirred suspension of aluminium trichloride (231 mg, 1.73 mmol) in toluene (7 ml) and the red brown suspension was refluxed for 1 hr. The solvent was removed under vacuum and the residue was partitioned between water (20 ml) and 10% ethanol/chloroform (2×100 ml). The organic layer was washed with brine and dried (Na$_2$SO$_4$). Removal of the solvent under vacuum gave 6-hydroxy-4-chlorocinnoline (154 mg) as a single component by TLC (1:1 ethylacetate/hexanes). $\delta_H$ (CD$_3$OD)=7.33 (d, 1H); 7.56 (dd, 1H); 8.32 (d, 1H) and 9.15 (br s 1H). MS (ESI) (M+H)$^+$ 181.

(c) Preparation of 6-{2-[(1-(6-methyl-3-pyridazinyl)-4-piperidinyl]ethoxy)}-4-chlorocinnoline A solution of DIAD (42 mg, 0.21 mmol) in THF (0.4 ml) was added slowly to a suspension containing 6-hydroxy-4-chlorocinnoline (30 mg, 0.17 mmol), triphenylphosphine (65 mg, 0.25 mmol) and 1-(6-methyl-3-pyridazinyl)-4-(2-hydroxyethyl)-piperidine (40 mg, 0.18 mmol) in THF (5 ml) and the suspension cleared. The reaction was left to stir overnight, then the reaction was adsorbed onto silica (1.5 g) and chromatography on silica gel (8 g) eluent ethylacetate gave the product (50 mg, 0.13 mmol) in 72% yield. $^1$H nmr $\delta_H$ (CD$_3$OD)=1.35 (m, 2H); 1.9 (m, 5H); 2.46 (s, 3H); 2.95 (m, 2H); 4.34 (m, 4H); 7.19 (d, 1H); 7.26 (d, 1H); 7.42 (d, 1H); 7.64 (dd, 1H); 8.34 (d 1H) and 9.24 (br s 1H). MS (ESI) (M+H)$^+$ 384.

(d) Preparation of Compound No 53

A solution of sodium ethoxide (0.3 mmol) in ethanol (0.15 ml) was added dropwise to a solution of the above (part c) 4-chlorocinnoline (23 mg, 60 μmol) in dry ethanol (3 ml) and the reaction was allowed to stir for 2 hr. The reaction was quenched with saturated ammonium chloride/brine (1 ml) and solvents removed under vacuum. The residue was partitioned between brine (5 ml) and 5% ethanol/ethylacetate (2×30 ml), dried (Na$_2$SO$_4$) and adsorbed onto silica (1 g) under vacuum. Chromatography on silica gel (8 g) eluent 5% methanol/ethylacetate gave Compound No 53 (15 mg, 38 μmol) in 63% yield.

Example 12

Preparation of 7-{2-[1-(6-methyl-3-pyridazinyl)-4-piperidinyl]ethoxy}-4-ethoxy-cinnoline (Compound 52 from Table 5)

4-Hydroxy-7-methoxy-cinnoline (Osborn, A. R. and Schofield, K. *J. Chem. Soc.* (1955) 2100) was prepared following a similar method to that described in Example 11 for the 6-isomer. This compound was converted to Compound 52 in a similar manner to that described in Example 11 for the 6-isomer. The $^1$H nmr and MS data are recorded in Table 6 below Example 13

Preparation of 7-{2-[1-(6-methyl-3-pyridazinyl)-4-piperidinyl]ethoxy}-4-ethoxy-quinazoline (Compound 51 from Table 5)

(a) Synthesis of 7-nitroquinazolin-4-one

A mixture of 4-nitroanthranilic acid (2.17 g, 11.91 mmol) and formamide (1.5 mL, 38.43 mmol) was heated at 165° C. for 4 hours. The warm reaction mixture was poured into ice/water (30 mL) and the resulting precipitate was collected via filtration, to give an orange solid (2.16 g, 95% yield) which was dried over P$_2$O$_5$. This was used without further purification.

$^1$H nmr; 8.24 (d, 1H), 8.32 (s, 1H), 8.34 (s, 1H), 8.35 (d, 1H).

(b) Synthesis of 7-Aminoquinazolin-4-one

Pd/C (100 mg) was added as a single portion to a degassed and flushed (3×Ar) suspension of 7-nitroquinazolin-4-one (1.15 g, 6.02 mmol) in methanol (150 mL). The resulting black mixture was degassed, flushed with hydrogen and allowed to stir for 4 hours. The mixture was filtered through celite, washed well with methanol, and the filtrate concentrated to give a tanned solid. This was purified by column chromatography (silica) using 10% methanol/ethyl acetate as the eluent. Combined fractions gave a beige solid (949 mg, 98% yield).

$^1$H nmr; 6.68 (s, 1H), 6.87 (d, 1H), 7.73 (d, 1H), 7.83 (s, 1H), 11.40 (bs, 1H).

(c) Synthesis of 7-Hydroxyquinazolin-4-one

A solution of sodium nitrite (1.40 g, 20.32 mmol) in water (17 mL) was added dropwise to a cooled suspension of 7-aminoquinazolin-4-one (712 mg, 4.42 mmol) in sulfuric acid/water (4.4 mL, 18 mL), keeping the temperature at approx. 0° C. The mixture was stirred at room temperature for 2 hours, diluted with water (15 mL) and heated at reflux for 15 minutes. The cooled mixture was neutralized and the precipitate was collected via filtration, and purified by column chromatography (silica) using 10% methanol/ethyl acetate as the eluent. The combined fractions gave an orange solid (541 mg, 76%).

$^1$H nmr; 6.85-6.91 (m, 2H), 7.87 (s, 1H), 7.92 (s, 1H).

(d) Synthesis of 7-Hydroxy-4-ethoxyquinazoline

A mixture of 7-hydroxyquinazolin-4-one (105 mg, 648 μmol), phosphorous oxychloride (2 ml), and dimethylaniline (85 μl, 671 μmol) was heated at reflux for 15 minutes in an argon atmosphere. The cooled mixture was concentrated under vacuum, and kept in an argon atmosphere to avoid hydrolysis. This residue was dissolved in ethanol (anhydrous, 3 mL), and a solution of sodium (283 mg, 12.34 mmol) in ethanol (3 ml) was added dropwise. The resulting yellow mixture was stirred at room temperature under argon for 2 hours, acidified to pH 6 using NaH$_2$PO$_4$ and extracted with ethyl acetate (3×50 mL). The combined extracts were dried (MgSO$_4$), filtered and concentrated. The white solid (156 mg) was used without further purification.

$^1$H nmr; 1.49 (t, 3H), 4.78 (q, 2H), 7.26 (d, 1H), 7.43 (s, 1H), 8.11 (d, 1H), 8.83 (s, 1H).

(e) Preparation of Compound No. 51

A mixture of 3-[4-(2-chloroethyl)-1-piperidinyl]-6-methylpyridazine (76 mg, 318 μmol), 7-hydroxy-4-ethoxyquinazoline (100 mg, 526 μmol), potassium carbonate (109 mg, 789 μmol) and potassium iodide (53 mg, 319 μmol) in DMF (5 mL) was heated at 90° C. overnight in an argon atmosphere. The mixture was concentrated, and the residue partitioned between ethyl acetate (100 mL) and water (20 mL). The organic phase was dried (MgSO$_4$), filtered, concentrated and purified by column chromatography (silica), using gradient elution (ethyl acetate-methanol/EA). The combined fractions gave a white solid (22 mg, 18%). The ¹H nmr data are recorded in Table 6 below.

Example 14

Compounds No 54 and 55 were prepared by reacting 3-[4-(2-chloroethyl)-1-piperidinyl]-6-methylpyridazine with the appropriate 6-hydroxyquinazoline following similar conditions to those described in Example 13, part (e). The ¹H nmr and/or MS data are recorded in Table 6 below.

Example 15

Preparation of 6-{2-[1-(6-methyl-3-pyridazinyl)-4-piperidinyl]ethoxy}-2-ethoxy-quinoxaline (Compound 43 from Table 4)

(a) Preparation of 2-chloro-6-hydroxyquinoxaline

Aluminium trichloride (85 mg, 638 µmol) was added as a single portion to a stirred mixture of 2-chloro-6-methoxyquinoxaline (73 mg, 375 µmol) and anhydrous toluene (3 ml) under an Argon atmosphere. The reaction mixture was heated at reflux for approx. 1 hr, then allowed to stir overnight at room temperature. Tlc (silica; 2:1 hexane/ethyl acetate) showed no remaining starting material and new polar material. Water (1 ml) and ice were added and the mixture stirred. The contents were partitioned between water (5 ml) and ethyl acetate (100 ml). The aqueous phase was extracted into ethyl acetate (50 ml), then the organic extracts combined and washed with water (10 ml), followed by brine (10 ml) and dried ($Na_2SO_4$). Concentration gave a brown solid, which was pre-adsorbed onto silica, then chromatographed on silica (9 g); eluent: 20% ethyl acetate in hexane then 25% ethyl acetate in hexane to give 2-chloro-6-hydroxyquinoxaline 54 mg (79%).

(b) Preparation of 2-chloro-6-{2-[1-(6-methyl-3-pyridazinyl)-4-piperidinyl]ethoxy}-quinoxaline A mixture of 2-chloro-6-hydroxyquinoxaline (52 mg, 288 µmol), 3-[-4-(2-chloroethyl)-1-piperidinyl]-6-methylpyridazine (76 mg, 317 µmol), potassium iodide (53 mg, 317 µmol) and potassium carbonate (199 mg, 1.44 mmol) in anhydrous dimethylformamide (2 ml) was heated at 90° under an Argon atmosphere for 2 days. Tlc (silica; ethyl acetate) showed new polar material. Removal of the solvent under high vacuum and then chromatography on silica (5 g; eluent: 30% hexane in ethyl acetate) gave the product as a white solid 68 mg (61%).

(c) Preparation of Compound 43

Sodium (78 mg, 3.39 mmol) was added portionwise to anhydrous ethanol (2 ml). The resulting sodium ethoxide solution was added to a stirred solution of the chloroquinoxaline from part (b) (65 mg, 169 µmol) in anhydrous tetrahydrofuran (2 ml) under an Argon atmosphere. The reaction mixture was heated at reflux for several hours then allowed to stir at room temperature overnight. The reaction mixture was quenched with saturated ammonium chloride solution (1 ml), then the contents partitioned between water (3 ml) and dichloromethane (50 ml). The aqueous phase was extracted into dichloromethane (50 ml), the organic extracts combined and washed with brine then dried ($Na_2SO_4$). The crude product was pre-adsorbed onto silica then chromatographed on silica (11 g; eluent 2:1 ethyl acetate/hexane) to give Compound 43 as a white solid (57 mg 86%).

Example 16

Compounds No 44, 45 and 46 were prepared by reacting 3-[4-(2-chloroethyl)-1-piperidinyl]-6-methylpyridazine or 2-[-1-(6-methyl-3-pyridazinyl)-4-piperidinyl]ethanol with the appropriate 6-hydroxyquinoxaline following similar conditions to those described in earlier examples. The ¹H nmr and/or MS data are recorded in Table 6 below.

Example 17

The compounds of the invention which are listed in Tables 1 to 5 were generally purified by chromatography on silica gel and were isolated as solids and characterised by ¹H nmr and mass spectroscopy. For convenience, the nmr and ms data are recorded in Table 6 below.

TABLE 6

| Compound No. | MS data (ESI) | NMR data: Proton Chemical Shift d in ppm ($CDCl_3$ unless otherwise noted) |
|---|---|---|
| 19 | 415 (M + 1)⁺ | 1.35 (m, 1H), 1.49 (t, 3H), 1.80-1.90 (m, 6H), 2.64 (s, 3H), 2.99 (m, 2H), 3.34 (q, 2H), 4.10 (t, 2H), 4.37 (m, 2H), 6.93 (dd, 1H), 7.05 (d, 1H), 7.21 (d, 1H), 7.38 (s, 1H), 7.59 (d, 1H). |
| 20 | 413 (M + 1)⁺ | 1.05 (t, 3H), 1.33 (m, 1H), 1.88 (m, 8H), 2.79 (s, 3H), 3.10 (m, 2H), 4.07 (t, 2H), 4.40 (m, 2H), 4.50 (t, 2H), 6.84 (dd, 1H), 7.22 (s, 1H), 7.25 (d, 1H), 7.42 (d, 1H), 7.48 (m, 1H) |
| 21 | 399 (M + 1)⁺ | 1.33 (m, 1H), 1.48 (t, 3H), 1.79 (m, 2H), 1.92 (m, 4H), 2.73 (s, 3H), 3.04 (m, 2H), 4.07 (t, 2H), 4.39 (m, 2H), 4.60 (q, 2H), 6.84 (dd, 1H), 7.22 (s, 1H), 7.25 (d, 1H), 7.36 (d, 1H), 7.48 (d, 1H) |
| 22 | Not recorded | 1.35 (m, 1H), 1.49 (t, 3H), 1.80-1.90 (m, 6H), 2.58 (s, 3H), 2.99 (m, 2H), 3.32 (q, 2H), 4.05 (t, 2H), 4.37 (m, 2H), 6.85 (dd, 1H), 6.95 (d, 1H), 7.1 (m, 2H), 7.35 (d, 1H). |
| 23 | Not recorded | 1.35 (m, 1H), 1.53 (t, 3H), 1.80-1.90 (m, 6H), 2.58 (s, 3H), 2.99 (m, 2H), 4.05 (t, 2H), 4.37 (m, 2H), 4.60 (q, 2H), 6.76 (dd, 1H), 6.95 (d, 1H), 7.0-7.1 (m, 2H), 7.15-7.25 (m, 2H). |
| 24 | 412 (M + 1)⁺ | 1.01 (t, 3H), 1.35 (m, 3H), 1.68-1.88 (m, 6H), 2.54 (s, 3H), 2.92 (m, 2H), 3.37 (t, 2H), 4.02 (t, 2H), 4.33 (m, 2H), 6.87-6.92 (m, 2H), 7.08 (d, 1H), 7.12 (s, 1H), 7.42 (d, 1H) |
| 25 | 398 (M + 1)⁺ | 1.31 (m, 1H), 1.39-1.42 (2 × t, 3H), 1.68-1.85 (m, 6H), 2.52 (s, 3H), 2.90 (m, 2H), 3.27-3.43 (2 × q, 2H), 4.02-4.14 (m, 2H), 4.25 (m, 2H), 6.75-6.85 (m, 1-2H), 6.95-7.21 (m, 3H) |

TABLE 6-continued

| Compound No. | MS data (ESI) | NMR data: Proton Chemical Shift d in ppm (CDCl$_3$ unless otherwise noted) |
|---|---|---|
| 26 | Not recorded | 0.98 (t, 3H); 1.25-1.55 (m, 3H), 1.80-1.95 (m, 6H), 2.61 (s, 3H), 2.85-3.0 (m, 4H), 4.06 (t, 2H), 4.37 (m, 2H), 6.88 (dd, 1H), 6.95-7.05 (m, 2H), 7.17 (d, 1H), 7.54 (d, 1H) |
| 27 | Not recorded | 1.06 (t, 3H); 1.35 (m, 1H), 1.80-1.95 (m, 8H), 2.61 (s, 3H), 2.85-3.0 (m, 4H), 4.06 (t, 2H), 4.37 (m, 2H), 6.88-6.94 (m, 2H), 7.03 (d, 1H), 7.10 (d, 1H), 7.54 (d, 1H) |
| 28 | Not recorded | 1.25-1.35 (m, 2H), 1.50 (t, 3H), 1.73-1.88 (m, 5H), 2.23 (s, 3H), 2.54 (s, 3H), 2.90 (t, 2H), 4.03 (t, 2H), 4.32-4.37 (m, 2H), 4.58 (q, 2H), 6.78-6.83 (m, 2H), 6.93 (fd, 1H), 7.32 (d, 1H) |
| 29 | Not recorded | 1.25-1.27 (m, 2H), 1.39 (t, 3H), 1.76-1.91 (m, 5H), 2.42 (s, 3H), 3.18 (t, 2H), 3.89-3.93 (m, 2H), 4.01 (t, 2H), 4.57 (q, 2H), 6.82 (dd, 1H), 6.92 (fd, 1H), 7.33 (d, 1H) |
| 30 | 398 (M + 1)$^+$ | 1.24-1.29 (m, 2H), 1.49 (t, 3H), 1.75-1.86 (m, 5H), 2.33 (s, 3H), 2.46 (s, 3H), 2.92 (t, 2H), 4.03 (t, 2H), 4.58 (q, 2H), 4.78-4.83 (m, 2H), 6.81 (dd, 1H), 6.92 (fd, 1H), 7.33 (d, 1H) |
| 31 | 373 (M + 1)$^+$ | 1.46-1.52 (m, 5H), 1.78-1.90 (m, 5H), 3.03 (t, 2H), 3.55-3.59 (m, 2H), 3.85 (s, 3H), 4.03 (t, 2H), 4.50 (q, 2H), 6.79 (dd, 1H), 6.91 (bd, 1H), 7.32 (d, 1H) |
| 32 | Not recorded | 1.39-1.43 (m, 2H), 1.50 (t, 3H), 1.77-2.00 (m, 5H), 2.36 (s, 3H), 3.08-3.14 (m, 2H), 4.01 (t, 2H), 4.45-4.49 (m, 2H), 4.57 (q, 2H), 6.79 (dd, 1H), 6.91 (bd, 1H), 6.98 (s, 1H), 7.35 (d, 1H) |
| 33 | Not recorded | 1.27-1.34 (m, 2H), 1.51 (s, 3H), 1.73-1.88 (m, 5H), 2.24 (s, 3H), 2.94 (t, 2H), 4.02 (t, 2H), 4.37-4.42 (m, 2H), 4.58 (q, 2H), 6.72 (bs, 1H), 6.83 (dd, 1H), 6.91 (fd, 1H), 7.33 (d, 1H), 8.39 (bs, 1H). |
| 34 | Not recorded | 1.45-1.55 (m, 5H), 1.69-1.82 (m, 4H), 2.23 (s, 3H), 2.72 (t, 2H), 3.93 (t, 2H), 4.57 (q, 2H), 5.79 (s, 1H), 6.77 (dd, 1H), 6.89 (fd, 1H), 7.31 (d, 1H) |
| 35 | 383 (M + 1)$^+$ | 1.34 (m, 1H); 1.50 (t, 3H); 1.80-1.95 (m, 6H); 2.74 (s, 3H); 3.05 (m, 2H); 4.08 (t, 2H); 4.40 (m, 2H); 4.46 (q, 2H); 6.85 (m, 2H); 7.24 (bd, 1H); 7.37 (bd, 1H); 7.47 (d, 1H) |
| 36 | 367 (M + 1)$^+$ | 1.34 (m, 2H), 1.43 (t, 3H), 1.82-1.94 (m, 5H), 2.74 (s, 3H), 2.96 (q, 2H), 3.05 (m, 2H), 4.10 (t, 2H), 4.40 (m, 2H), 6.89 (dd, 1H), 6.97 (fd, 1H), 7.22 (d, 1H), 7.35 (d, 1H), 7.50 (d, 1H) |
| 37 | 403 (M + 1)$^+$ | 1.37 (m, 1H), 1.50 (t, 3H), 1.91 (m, 4H), 3.03 (bt, 2H), 4.08 (t, 2H), 4.39 (bd, 2H), 4.46 (q, 2H), 6.82-6.86 (m, 2H), 6.97 (bd, 1H), 7.21 (bd, 1H), 7.47 (d, 1H) |
| 38 | 397 (M + 1)$^+$ | 1.06 (t, 3H), 1.34 (m, 3H), 1.81-1.97 (m, 6H), 2.72 (s, 3H), 3.12 (m, 2H), 4.08 (t, 2H), 4.36 (t, 2H), 6.84 (m, 2H), 7.24 (m, 1H), 7.41-7.49 (m, 2H) |
| 39 | 381 (M + 1)$^+$ | 1.03 (t, 3H), 1.35 (m, 2H), 1.81-1.94 (m, 7H), 2.69 (s, 3H), 2.90 (t, 2H), 3.03 (t, 2H), 4.10 (t, 2H), 4.36 (m, 2H), 6.89 (bd, 1H), 6.96 (s, 1H), 7.14 (bd, 1H), 7.29 (bd, 1H), 7.49 (bd, 1H) |
| 40 | 399 (M + 1)$^+$ | 1.36 (m, 2H), 1.48 (t, 3H), 1.79-1.91 (m, 5H), 2.60 (s, 3H), 2.97 (dt, 2H), 4.11 (t, 2H), 4.36 (m, 2H), 4.56 (q, 2H), 6.95 (dd, 1H), 6.99 (bd, 1H), 7.14 (fd, 1H), 7.16 (bd, 1H), 7.76 (bd, 1H) |
| 41 | Not recorded | 1.30-1.34 (m, 2H), 1.48 (t, 3H), 1.60-1.70 (m, 1H), 1.84-1.91 (m, 4H), 3.04 (t, 2H), 4.01 (t, 2H), 4.39-4.49 (m, 4H), 6.82-6.86 (m, 2H), 6.99 (d, 1H), 7.23 (d, 1H), 7.47 (d, 1H) |
| 42 | 384 (M + 1)$^+$ | 1.43 (t, 3H), 2.46 (s, 3H), 2.76 (t, 4H), 2.93 (t, 2H), 3.62 (t, 4H), 4.18 (t, 2H), 4.38 (q, 2H), 6.8 (m, 2H), 6.89 (d, 1H), 7.09 (d, 1H), 7.42 (d, 1H) |
| 43 | Not recorded | 1.37 (m, 1H), 1.46 (t, 3H), 1.85-1.92 (m, 6H), 2.66 (s, 3H), 3.01 (t, 2H), 4.16 (t, 2H), 4.38 (m, 2H), 4.51 (q, 2H), 7.08 (bd, 1H), 7.22-7.26 (m, 1H), 7.32 (m, 1H), 7.34 (fd, 1H), 7.72 (d, 1H), 8.40 (s, 1H) |
| 44 | 418 (M + 1)$^+$ | 1.37 (m, 1H), 1.86-1.96 (m, 6H), 2.74 (s, 3H), 3.06 (t, 2H), 4.19 (t, 2H), 4.41 (m, 2H), 7.22 (bd, 1H), 7.29 (fd, 1H), 7.35 (bd, 1H), 7.43 (dd, 1H), 7.91 (d, 1H) |
| 45 | Not recorded | 1.36 (m, 1H), 1.50 (2 × t, 6H), 1.80-1.94 (m, 6H), 2.68 (s, 3H), 3.02 (m, 2H), 4.13 (t, 2H), 4.38 (m, 2H), 4.59 (2 × q, 4H), 7.09 (dd, 1H), 7.11-7.15 (m, 1H), 7.15 (fd, 1H), 7.27 (bd, 1H), 7.62 (d, 1H) |
| 46 | 394 (M + 1)$^+$ | 1.37 (m, 2H), 1.47 (t, 3H), 1.82-1.95 (m, 5H), 2.69 (s, 3H), 3.03 (m, 2H), 4.18 (t, 2H), 4.39 (m, 2H), 4.52 (q, 2H), 7.13 (bd, 1H), 7.15 (s, 1H), 7.15-7.19 (m, 1H), 7.27 (bd, 1H), 7.87 (d, 1H), 8.29 (s, 1H) |
| 47 | Not recorded | 1.50 (t, 3H), 1.55-1.89 (m, 5H), 2.99 (t, 2H), 3.96 (t, 3H), 4.35-4.39 (m, 2H), 4.56 (q, 2H), 6.79 (dd, 1H), 6.91-6.96 (m, 2H), 7.21 (d, 1H), 7.35 (d, 1H) |
| 48 | 384 (M + 1)$^+$ | 1.49 (t, 3H), 2.54 (s, 3H), 2.81 (m, 4H), 2.95 (t, 2H), 3.71 (m, 4H), 4.21 (t, 2H), 4.58 (q, 2H), 6.84 (dd, 1H), 6.86 (d, 1H), 6.95 (fd, 1H), 7.09 (bd, 1H), 7.34 (bd, 1H) |
| 49 | Not recorded | 1.46-1.57 (m, 5H), 1.73-1.85 (m, 4H), 2.25 (s, 3H), 2.73 (t, 2H), 3.99 (t, 2H), 4.45 (q, 2H), 5.80 (s, 1H), 6.81-6.84 (m, 2H), 7.43 (d, 1H). |

TABLE 6-continued

| Compound No. | MS data (ESI) | NMR data: Proton Chemical Shift d in ppm (CDCl$_3$ unless otherwise noted) |
|---|---|---|
| 50 | Not recorded | 1.42-1.44 (m, 2H), 1.49 (t, 3H), 1.79-1.86 (m, 5H), 2.56 (s, 3H), 3.08-3.15 (m, 2H), 3.91-3.94 (m, 2H), 4.06 (t, 2H), 4.45 (q, 2H), 6.82-6.85 (m, 2H), 7.45 (d, 1H) |
| 51 | Not recorded | 1.22-1.37 (m, 2H), 1.48 (t, 3H), 1.51-1.88 (m, 3H), 2.53 (s, 3H), 2.93 (t, 2H), 4.14 (t, 2H), 4.31-4.35 (m, 2H), 4.59 (q, 2H), 6.88 (d, 1H), 7.06 (d, 1H), 7.13 (d, 1H), 7.22 (d, 1H), 8.04 (d, 1H), 8.69 (s, 1H) |
| 52 | 394 (M + H)$^+$ | (CD$_3$OD) 1.4 (m, 2H); 1.62 (t, 3H); 1.93 (m, 5H); 2.51 (s, 3H); 2.99 (m, 2H); 4.35 (m, 4H); 4.52 (q, 2H); 7.24 (d, 1H); 7.31 (d, 1H); 7.47 (dd, 1H); 7.64 (d, 1H); 8.19 (d, 1H) and 8.99 (br s 1H) |
| 53 | 394 (M + H)$^+$ | (CD$_3$OD) 1.3 (m, 2H); 1.62 (t, 3H); 1.93 (m, 5H); 2.51 (s, 3H); 2.99 (m, 2H); 4.32 (m, 2H); 4.38 (m, 2H); 4.52 (q, 2H); 7.23 (d, 1H); 7.31 (d, 1H); 7.47 (d, 1H); 7.58 (dd, 1H); 8.27 (d, 1H) and 8.95 (br s 1H) |
| 54 | Not recorded | 1.31-1.43 (m, 2H), 1.52 (t, 3H), 1.82-1.91 (m, 3H), 2.55 (s, 3H), 2.95 (t, 2H), 4.16 (t, 2H), 4.32-4.37 (m, 2H), 4.65 (q, 2H), 6.87-6.93 (m, 1H), 7.05-7.11 (m, 1H), 7.39 (s, 1H), 7.45 (d, 1H), 7.84 (d, 1H), 8.67 (s, 1H) |
| 55 | Not recorded | 1.29-1.33 (m, 2H), 1.42-1.53 (m, 6H), 1.78-1.89 (m, 5H), 2.52 (s, 3H), 2.93 (t, 2H), 4.08-4.14 (m, 2H), 4.31-4.35 (m, 2H), 4.44 (q, 2H), 4.63 (q, 2H), 6.89 (d, 1H), 7.06 (d, 1H), 7.32-7.37 (m, 2H), 7.58 (d, 1H) |
| 56 | 384 (M + 1)$^+$ | 1.34-1.38 (m, 2H), 1.36 (t, 3H), 1.79-1.89 (m, 5H), 2.59 (s, 3H), 2.96 (dt, 2H), 4.02 (q, 2H), 4.08 (t, 2H), 4.36 (m, 2H), 6.64 (fd, 1H), 6.81 (dd, 1H), 6.98 (bd, 1H), 7.15 (bd, 1H), 7.67 (d, 1H) |
| 57 | 397 (M + 1)$^+$ | 0.98 (t, 3H), 1.35 (m, 2H), 1.78-1.96 (m, 7H), 2.78 (s, 3H), 3.08 (t, 2H), 3.95 (t, 2H), 4.09 (t, 2H), 4.41 (m, 2H), 6.64 (fd, 1H), 6.81 (dd, 1H), 7.50 (bd, 1H), 7.41 (bd, 1H), 7.69 (d, 1H) |
| 58 | Not recorded | 0.96 (t, 3H), 1.4 (m, 3H), 1.68-1.88 (m, 6H), 2.11 (q, 2H), 2.52 (s, 3H), 2.92 (m, 2H), 4.06 (t, 2H), 4.33 (m, 2H), 4.60 (t, 2H), 6.86 (d, 1H), 7.0-7.1 (m, 3H), 7.08 (d, 1H), 7.70 (d, 1H) |

Example 18

Anti-HRV Activity in Mammalian Cell Culture Assays Inhibition of Viral Cytopathic Effect (CPE) and Measurement of Cytotoxicity The ability of compounds to suppress virus replication and thereby protect cells from HRV-induced CPE was measured using human embryo lung (MRC-5 cells infected with HRV type 1A. Cells grown in 96 well tissue culture plates using conventional mammalian tissue culture medium (such as minimum essential medium) supplemented with fetal calf serum were used in an assay essentially similar to that described by Sidwell and Huffman (*Applied Microbiology*, 22, 797-801 (1971)). Test compounds were dissolved in 100% anhydrous dimethyl sulfoxide and serially diluted in tissue culture medium. The antiviral potency of the test compounds was assessed by exposing replicate tissue culture wells to a selected dilution series of between 6 and 7 compound concentrations in the presence of sufficient test virus to invoke significant CPE over the course of the assay. Control cells were also exposed to identical concentrations of compounds in the absence of virus or were infected with virus under the same conditions but in the absence of compounds. Compounds of established anti-HRV efficacy (enviroxime, ribavirin and pirodavir) were assayed by identical procedures in parallel to the test compounds. Tissue culture media were identically supplemented to maintain cell viability and support viral growth while suppressing bacterial growth over the period of the assay (supplements: 2% fetal calf serum, 0.01% sodium bicarbonate, 50 µg/ml gentamicin, 5 µM magnesium chloride, 10 mM of zinc chloride). The assays were incubated at 37° C. in a 5% CO$_2$ atmosphere until significant CPE was observed by microscopic examination of the untreated, HRV infected control cells (generally between 5 and 8 days). At this time all infected cultures were examined by eye using a light microscope and CPE scored on a scale of 0 (no CPE) to 4 (maximum CPE). Uninfected treated cultures were similarly scored for cytotoxic effects (e.g., cell enlargement, granularity, rounding, detachment). These scores were used to generate EC$_{50}$ (concentration of compound yielding 50% antiviral efficacy) and CC$_{50}$ (concentration of compound yielding 50% cytotoxicity) values by line regression analysis from plots of compound concentration versus % CPE or % cytotoxicity, respectively. As an alternative to a CC$_{50}$ value, cytotoxicity in some cases was expressed as the Minimum Toxic Concentration (MTC). The MTC corresponds to the lowest compound concentration at which cytotoxic effects were observed.

In some cases the visual scoring system described above was validated by vital dye staining to measure cell viability. The vital dye technique used was a modification of the method described by McManus (*Appl. Environment. Microbiol.*, 31, 35-38, 1976). After the assay had been scored by eye with the aid of a microscope, 100 µl of neutral red (NR) solution (0.34% NR in phosphate buffered saline (PBS)) was added to each well and mixed gently. The assays were returned to the 37° C. incubator for 2 hours to facilitate uptake of the NR by viable cells. The medium/NR mixture was then aspirated from the surface of the cells, which were washed twice with PBS. 0.25 ml of absolute ethanol containing Sorensen's citrate buffer I, was added with gentle mixing and the assays incubated at room temperature in the dark for 30 minutes to dissolve the NR. NR staining of viable cells was then quantified spectrophotometrically by measuring the color density of the NR solution using a BioTek EL-309 microplate reader at dual wavelengths of 540 and 405 nm. The differences in the two readings were automatically determined to eliminate background errors. EC$_{50}$ and CC$_{50}$ values were determined by regression analysis matching compound concentration to NR staining.

The results are shown in the Tables 7 and 8 below. Selectivity indices (SI) are the $CC_{50}$ or MTC divided by the $EC_{50}$. Tables 7 and 8 also show $IC_{50}$ data for the testing of the compounds of the invention against HRV strains 2 and 14. These results were obtained using a similar CPE method to that described above for HRV1A.

TABLE 7

| Compound No | $IC_{50}$ (μg/ml) HRV1A | $CC_{50}$ | $IC_{50}$ (μg/ml) HRV2 | HRV14 |
|---|---|---|---|---|
| 1 | 0.179 | >1 | >0.50 | >0.50 |
| 2 | 0.120 | >1 | >0.50 | >0.50 |
| 3 | 0.060 | >1 | 0.144 | 0.130 |
| 4 | 0.006 | >1 | 0.099 | 0.047 |
| 5 | | | 0.003 | 0.007 |
| 6 | | | 0.067 | 0.146 |
| 7 | | | 0.002 | 0.006 |
| 8 | | | 0.008 | 0.020 |
| 9 | | | 0.061 | 0.056 |
| 10 | | | 0.065 | 0.056 |
| 11 | | | 0.002 | 0.020 |
| 12 | | | 0.159 | 0.099 |
| 13 | | | 0.004 | 0.015 |
| 14 | | | 0.024 | 0.006 |
| 15 | | | 0.007 | 0.006 |

TABLE 8

| Compound No | $IC_{50}$ (μg/ml) HRV2 | HRV14 |
|---|---|---|
| 16 | 0.10 | 0.169 |
| 19 | 0.165 | 0.049 |
| 20 | 0.166 | 0.041 |
| 21 | 0.104 | 0.014 |
| 22 | 0.004 | 0.050 |
| 23 | 0.045 | — |
| 24 | 0.131 | >0.250 |
| 26 | 0.130 | 0.082 |
| 27 | 0.075 | 0.028 |
| 28 | 0.101 | 0.040 |
| 30 | >0.250 | 0.198 |
| 31 | 0.237 | >0.250 |
| 32 | 0.012 | 0.039 |
| 33 | 0.167 | 0.166 |
| 34 | 0.209 | 0.118 |
| 35 | 0.001 | 0.005 |
| 36 | 0.024 | 0.088 |
| 37 | 0.003 | 0.019 |
| 38 | 0.003 | 0.029 |
| 39 | 0.084 | 0.013 |
| 40 | 0.003 | 0.029 |
| 41 | 0.003 | 0.009 |
| 43 | 0.012 | 0.012 |
| 46 | 0.084 | 0.013 |
| 47 | 0.004 | 0.010 |
| 48 | 0.069 | 0.011 |
| 49 | 0.035 | 0.012 |
| 50 | 0.007 | 0.005 |
| 51 | 0.027 | 0.120 |
| 52 | 0.190 | 0.200 |
| 56 | 0.246 | >0.250 |
| 57 | 0.133 | 0.237 |
| 58 | 0.032 | 0.139 |

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The invention claimed is:

1. A composition comprising a compound of formula II:

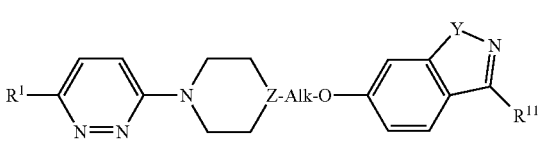

II wherein:
R$^1$ is hydrogen, $C_{1-4}$alkyl, halo, hydroxyl, mercapto, trifluoromethyl, amino, mono or di($C_{1-4}$alkyl)amino, cyano, formyl, —CH═NO—$C_{1-4}$alkyl, $C_{1-4}$alkoxy, $C_{1-4}$haloalkoxy, aryloxy, $C_{1-4}$alkylthio, or aryl;
Y is O, S, NH or NMe;
Z is CH or N;
Alk is $C_{1-6}$alkylene; and
R$^{11}$ is OR$^{10}$ or SR$^{10}$, where R$^{10}$ is $C_{1-4}$alkyl;
or a pharmaceutically acceptable salt thereof, together with a pharmaceutically acceptable carrier.

2. A composition comprising a compound of formula III:

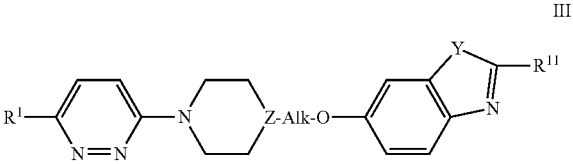

III wherein:
R$^1$ is hydrogen, $C_{1-4}$alkyl, halo, hydroxyl, mercapto, trifluoromethyl, amino, mono or di($C_{1-4}$alkyl)amino, cyano, formyl, —CH═NO—$C_{1-4}$alkyl, $C_{1-4}$alkoxy, $C_{1-4}$haloalkoxy, aryloxy, $C_{1-4}$alkylthio, or aryl;
Y is O, S, NH or NMe;
Z is CH or N;
Alk is $C_{1-6}$alkylene; and
R$^{11}$ OR$^{10}$ or SR$^{10}$, where R$^{10}$ is $C_{1-4}$alkyl;
or a pharmaceutically acceptable salt thereof, together with a pharmaceutically acceptable carrier.

3. A composition comprising a compound of formula V:

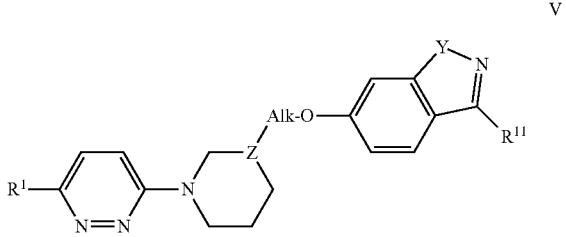

V wherein:
R$^1$ is hydrogen, $C_{1-4}$alkyl, halo, hydroxyl, mercapto, trifluoromethyl, amino, mono or di($C_{1-4}$alkyl)amino, cyano, formyl, —CH═NO—$C_{1-4}$alkyl, $C_{1-4}$alkoxy, $C_{1-4}$haloalkoxy, aryloxy, $C_{1-4}$alkylthio, or aryl;
Y is O, S, NH or NMe;

Z is CH or N;
Alk is $C_{1-6}$alkylene; and
$R^{11}$ is $OR^{10}$ or $SR^{10}$, where $R^{10}$ is $C_{1-4}$alkyl;
or a pharmaceutically acceptable salt thereof, together with a pharmaceutically acceptable carrier.

4. A composition comprising a compound of formula VI:

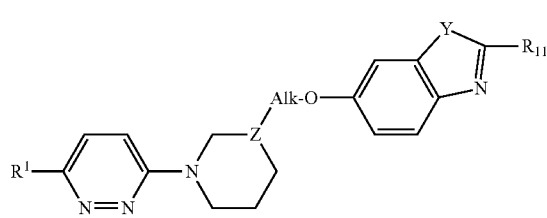

VI wherein:
- $R^{11}$ is hydrogen, $C_{1-4}$alkyl, halo, hydroxyl, mercapto, trifluoromethyl, amino, mono or di($C_{1-4}$alkyl)amino, cyano, formyl, —CH=NO—$C_{1-4}$alkyl, $C_{1-4}$alkoxy, $C_{1-4}$haloalkoxy, aryloxy, $C_{1-4}$alkylthio, or aryl;
- Y is O, S, NH or NMe;
- Z is CH or N;
- Alk is $C_{1-6}$alkylene; and
- $R^{11}$ is $OR^{10}$ or $SR^{10}$, where $R^{10}$ is $C_{1-4}$alkyl;

or a pharmaceutically acceptable salt thereof, together with a pharmaceutically acceptable carrier.

5. The composition according to claim 1, wherein the compound is selected from the group consisting of:

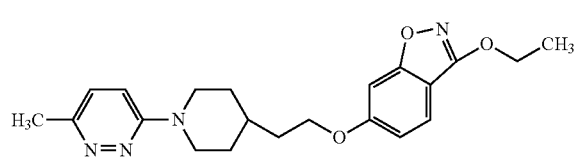

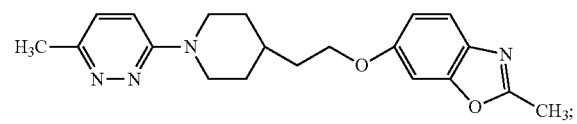

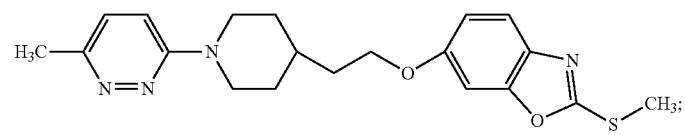

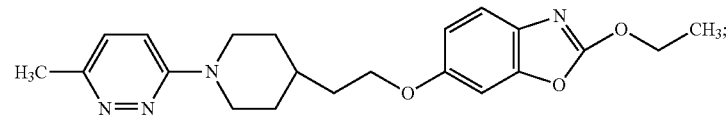

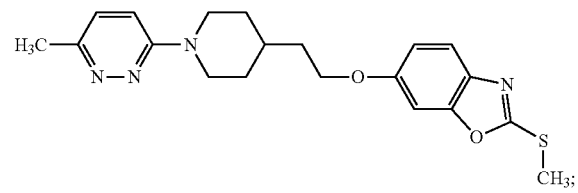

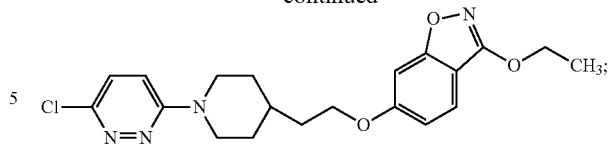

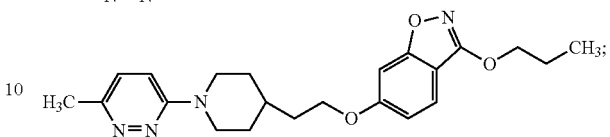

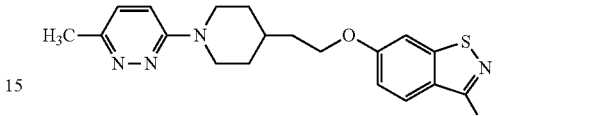

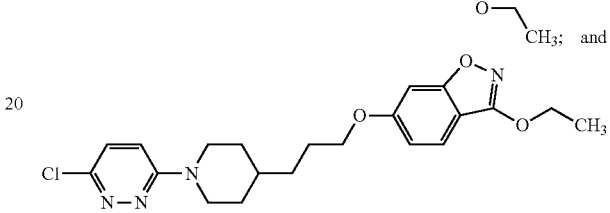

or a pharmaceutically acceptable salt thereof.

6. The composition according to claim 1, wherein the compound is:

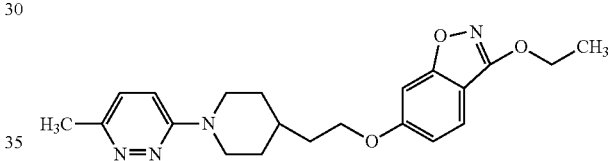

or a pharmaceutically acceptable salt thereof.

7. The composition according to claim 2, wherein the compound is selected from the group consisting of:

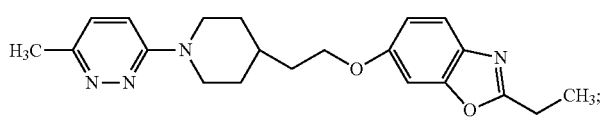

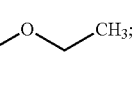

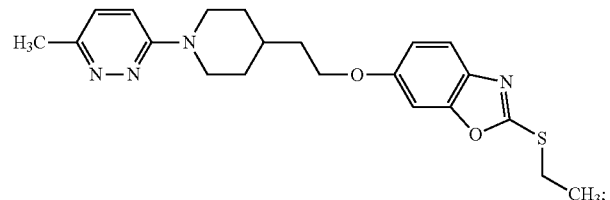

-continued

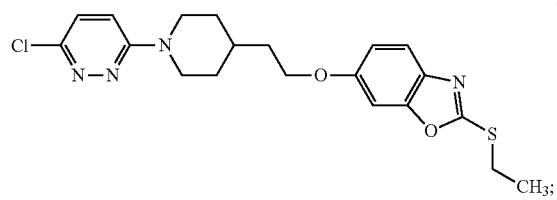
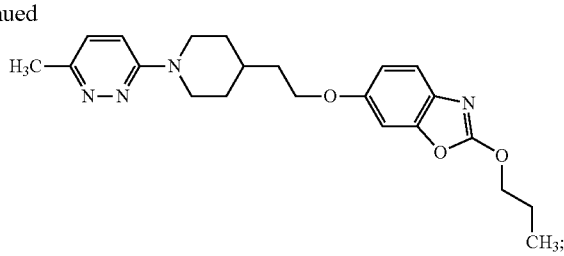
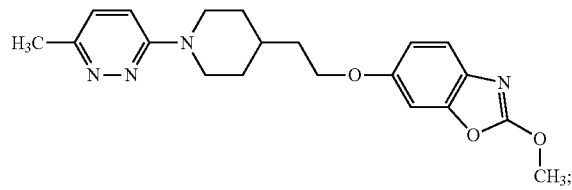
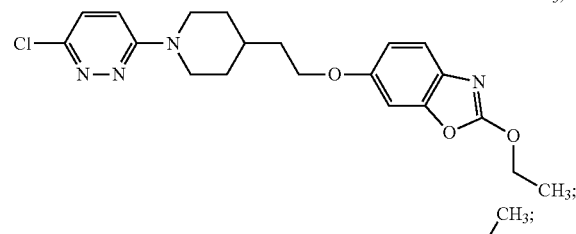
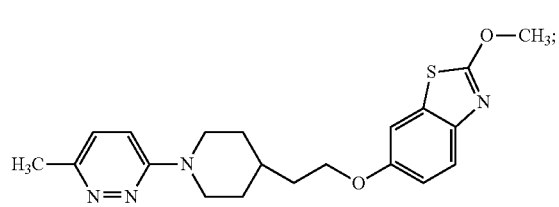
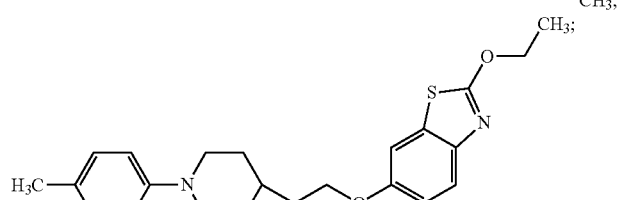
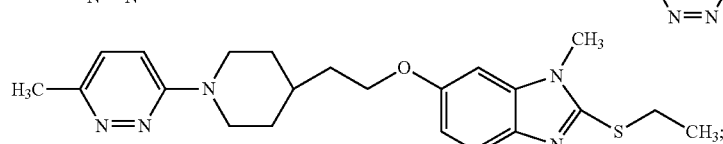
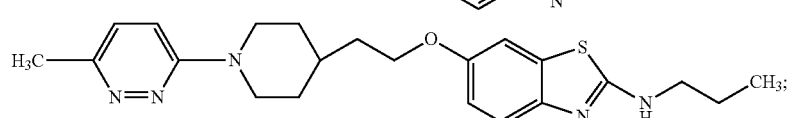
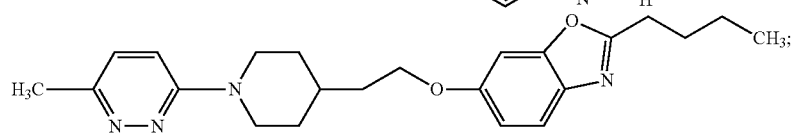
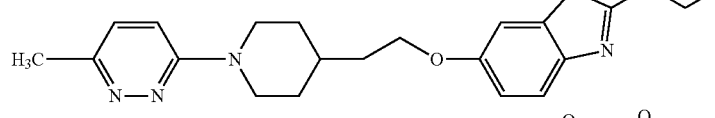
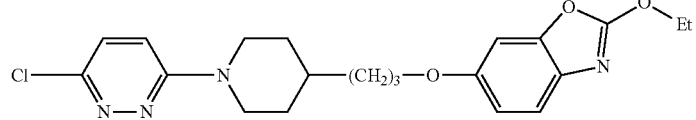
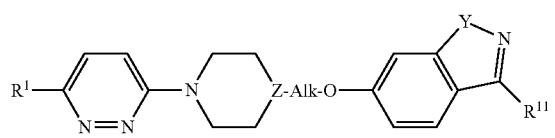

or a pharmaceutically acceptable salt thereof.

8. A method for the treatment of a human rhinovirus (HRV) infection in a respiratory tract of a mammal, comprising administering to the mammal an effective amount of a composition comprising a compound of formula II:

II

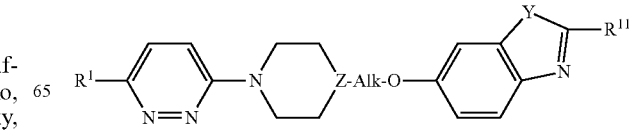

wherein:
$R^1$ is hydrogen, $C_{1-4}$alkyl, halo, hydroxyl, mercapto, trifluoromethyl, amino, mono or di($C_{1-4}$alkyl)amino, cyano, formyl, —CH=NO—$C_{1-4}$alkyl, $C_{1-4}$alkoxy, $C_{1-4}$haloalkoxy, aryloxy, $C_{1-4}$alkylthio, or aryl;

Y is O, S, NH or NMe;
Z is CH or N;
Alk is $C_{1-6}$alkylene; and
$R^{11}$ is $OR^{10}$ or $SR^{10}$, where $R^{10}$ is $C_{1-4}$alkyl;
or a pharmaceutically acceptable salt thereof, together with a pharmaceutically acceptable carrier.

9. A method for the treatment of a human rhinovirus (HRV) infection in a respiratory tract of a mammal, comprising administering to the mammal an effective amount of a composition comprising a compound of formula III:

III wherein:
R$^1$ is hydrogen, C$_{1-4}$alkyl, halo, hydroxyl, mercapto, trifluoromethyl, amino, mono or di(C$_{1-4}$alkyl)amino, cyano, formyl, —CH=NO—C$_{1-4}$alkyl, C$_{1-4}$alkoxy, C$_{1-4}$haloalkoxy, aryloxy, C$_{1-4}$alkylthio, or aryl;
Y is O, S, NH or NMe;
Z is CH or N;
Alk is C$_{1-6}$alkylene; and
R$^{11}$ is OR$^{10}$ or SR$^{10}$, where R$^{10}$ is C$_{1-4}$alkyl;
or a pharmaceutically acceptable salt thereof, together with a pharmaceutically acceptable carrier.

10. A method for the treatment of a human rhinovirus (HRV) infection in a respiratory tract of a mammal, comprising administering to the mammal an effective amount of a composition comprising a compound of formula V:

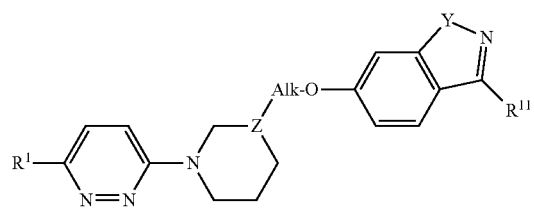

wherein:
R$^1$ is hydrogen, C$_{1-4}$alkyl, halo, hydroxyl, mercapto, trifluoromethyl, amino, mono or di(C$_{1-4}$alkyl)amino, cyano, formyl, —CH=NO—C$_{1-4}$alkyl, C$_{1-4}$alkoxy, C$_{1-4}$haloalkoxy, aryloxy, C$_{1-4}$alkylthio, or aryl;
Y is O, S, NH or NMe;
Z is CH or N;
Alk is C$_{1-6}$alkylene; and
R$^{11}$ is OR$^{10}$ or SR$^{10}$, where R$^{10}$ is C$_{1-4}$alkyl;
or a pharmaceutically acceptable salt thereof, together with a pharmaceutically acceptable carrier.

11. A method for the treatment of a human rhinovirus (HRV) infection in a respiratory tract of a mammal, comprising administering to the mammal an effective amount of a composition comprising a compound of formula VI:

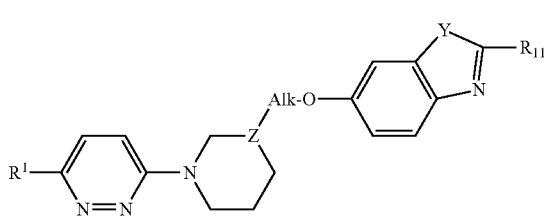

wherein:
R$^1$ is hydrogen, C$_{1-4}$alkyl, halo, hydroxyl, mercapto, trifluoromethyl, amino, mono or di(C$_{1-4}$alkyl)amino, cyano, formyl, —CH=NO—C$_{1-4}$alkyl, C$_{1-4}$alkoxy, C$_{1-4}$haloalkoxy, aryloxy, C$_{1-4}$alkylthio, or aryl;
Y is O, S, NH or NMe;
Z is CH or N;
Alk is C$_{1-6}$alkylene; and
R$^{11}$ is OR$^{10}$ or SR$^{10}$, where R$^{10}$ is C$_{1-4}$alkyl;
or a pharmaceutically acceptable salt thereof, together with a pharmaceutically acceptable carrier.

12. The method according to claim 8 wherein the compound is selected from the group consisting of:

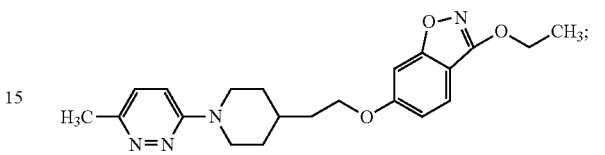

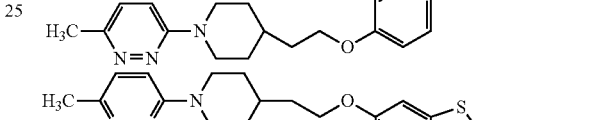

or a pharmaceutically acceptable salt thereof

13. The method according to claim 8 wherein the compound is:

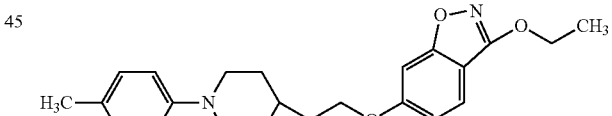

or a pharmaceutically acceptable salt thereof.

14. The method according to claim 9, wherein the compound is selected from the group consisting of:

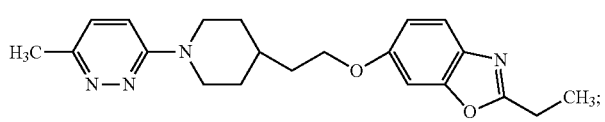

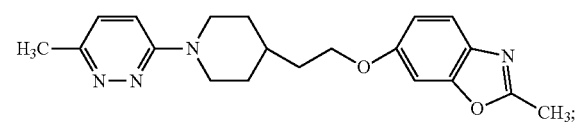

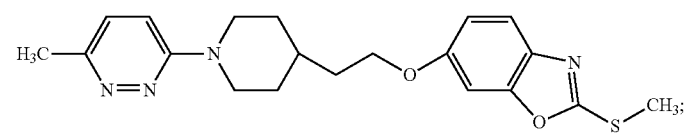

-continued
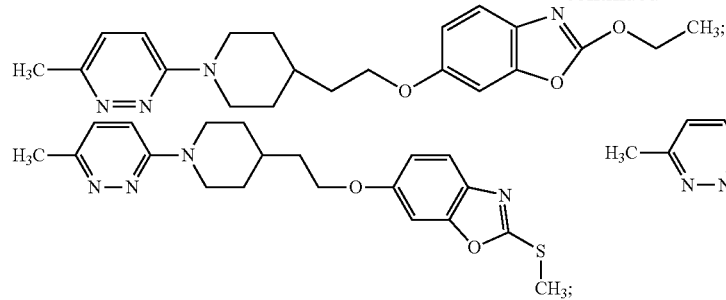
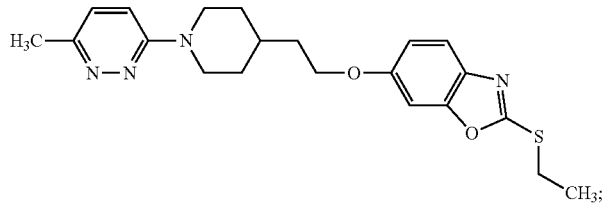
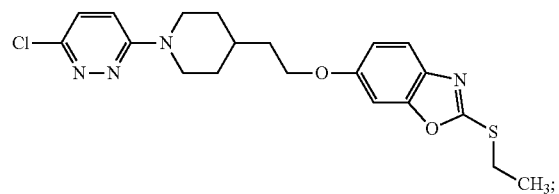
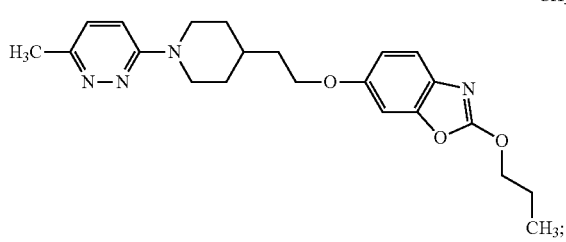
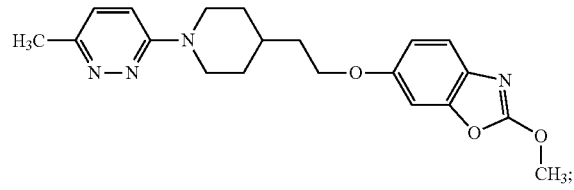
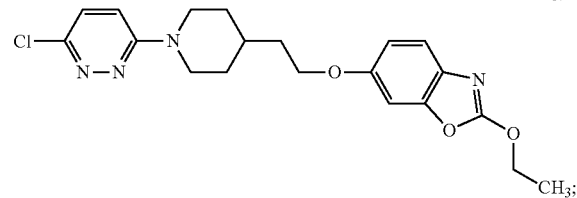
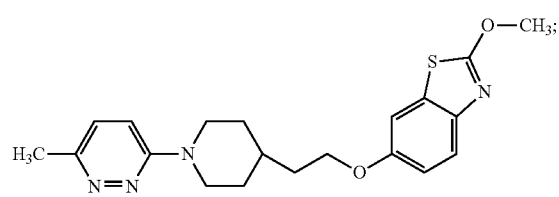
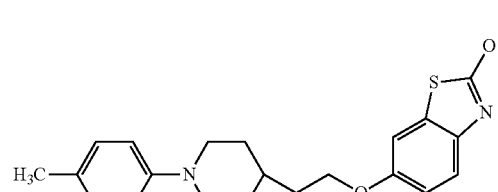
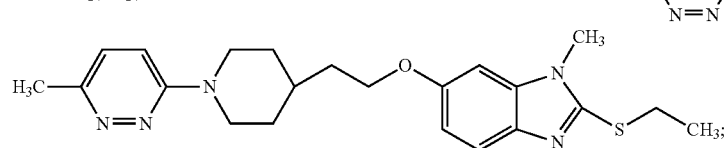
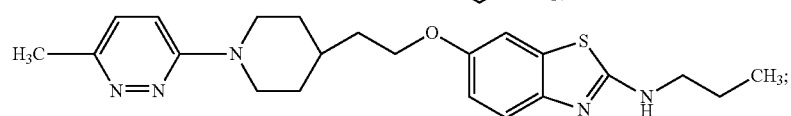
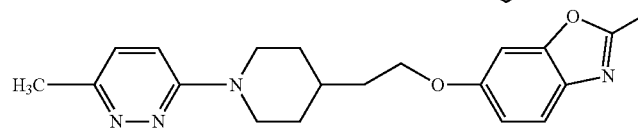
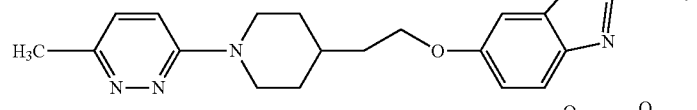
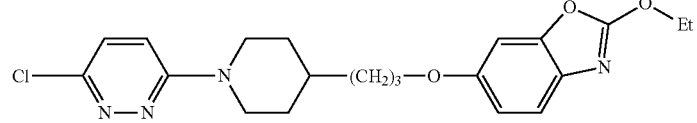
or a pharmaceutically acceptable salt thereof.
* * * * *